United States Patent
Bajcsy et al.

(10) Patent No.: US 9,060,714 B2
(45) Date of Patent: Jun. 23, 2015

(54) SYSTEM FOR DETECTION OF BODY MOTION

(75) Inventors: Ruzena Bajcsy, Berkeley, CA (US); Allen Y. Yang, Berkeley, CA (US); S. Shankar Sastry, Berkeley, CA (US); Roozbeh Jafari, Richardson, TX (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 921 days.

(21) Appl. No.: 12/631,714

(22) Filed: Dec. 4, 2009

(65) Prior Publication Data

US 2010/0176952 A1    Jul. 15, 2010

Related U.S. Application Data

(60) Provisional application No. 61/119,861, filed on Dec. 4, 2008.

(51) Int. Cl.
*G08B 23/00* (2006.01)
*G08B 21/00* (2006.01)
(Continued)

(52) U.S. Cl.
CPC .............. *A61B 5/1112* (2013.01); *A61B 5/11* (2013.01); *A61B 5/1117* (2013.01); *A61B 5/6804* (2013.01); *A61B 5/6824* (2013.01);
(Continued)

(58) Field of Classification Search
CPC ............ A61B 2562/0219; A61B 5/0002; A61B 5/0024; A61B 5/0205; A61B 5/1121; A61B 5/1123; A61B 5/1125; G08B 25/10; G08B 21/22; G08B 23/00; G01C 21/16; A63B 24/00; A63B 24/0062

USPC .......... 340/573.1, 669–671, 286.01, 539.12, 340/539.1, 286.07, 573.7; 702/141, 160, 702/179, 189; 434/247, 257
See application file for complete search history.

(56) References Cited

U.S. PATENT DOCUMENTS 6,287,253 B1 *    9/2001    Ortega et al. ................. 600/300
7,238,159 B2 *    7/2007    Banet et al. .................. 600/485
(Continued)

OTHER PUBLICATIONS

Yang et al. "Distributed Segmentation and Classification of Human Action Using a Wearable Motion Sensor Network", pp. 1-8, 2008.
(Continued)

*Primary Examiner* — Hung T Nguyen
(74) *Attorney, Agent, or Firm* — John P. O'Banion

(57) ABSTRACT

Methods for classifying aggregated data in a distributed sensor system are provided and illustrated with a wearable motion sensor network. The classification is operated in a distributed fashion on individual sensor nodes and a base station computer. The method classifies actions using a set of training motion sequences as prior examples and may reject outlying actions that are not in the training categories. Acquired sensor data is processed at the node by taking projections of the data to reduce dimensionality, calculating sparse representations of features using training sequences; validating and classifying local measurements and then transmitting classified measurements to a network base station. The base station aggregates local sensor measurements and performs a global classification of the data by forming global features from the local measurements; calculating sparse representations of global features; validating and classifying valid global features; and labeling global features and their corresponding local features.

12 Claims, 16 Drawing Sheets

(51) Int. Cl.
  *A61B 5/11*   (2006.01)
  *A61B 5/00*   (2006.01)

(52) U.S. Cl.
  CPC ............ *A61B 5/6828* (2013.01); *A61B 5/6829* (2013.01); *A61B 5/6887* (2013.01); *A61B 2562/0219* (2013.01); *A61B 5/7232* (2013.01); *A61B 5/6823* (2013.01)

(56) References Cited

U.S. PATENT DOCUMENTS

| | | | |
|---|---|---|---|
| 7,334,472 B2* | 2/2008 | Seo et al. | 73/379.01 |
| 7,640,804 B2* | 1/2010 | Daumer et al. | 73/510 |
| 7,827,000 B2* | 11/2010 | Stirling et al. | 702/141 |
| 7,927,253 B2* | 4/2011 | Vincent et al. | 482/9 |
| 8,277,387 B2* | 10/2012 | Muehlsteff et al. | 600/490 |
| 2001/0048368 A1* | 12/2001 | Lehrman et al. | 340/669 |
| 2007/0250286 A1* | 10/2007 | Duncan et al. | 702/139 |
| 2008/0164979 A1* | 7/2008 | Otto | 340/286.01 |
| 2008/0183090 A1* | 7/2008 | Farringdon et al. | 600/509 |
| 2008/0252445 A1* | 10/2008 | Kolen | 340/539.16 |

OTHER PUBLICATIONS

Yang et al. "Distributed Recognition of Human Actions Using Wearable Motion Sensor Networks" Journal of Ambient Intelligence and Smart Enviromnets 1 (2009) 1-5 IOS Press, pp. 1-13.

Yang et al.."Distributed Segmentation and Classification of Human Actions Using a Wearable Motion Sensor Network" Electrical Engineering & Computer Sciences, University of CA @ Berkeley, Dec. 6, 2007 pp. 1-19.

Kuryloski et al. "Dexternet: An Open Platform for Heterogeneous Body Sensor Networks and Its Applcaitons" IPSN'09 San Francisco, CA USA pp. 11-11, 2009.

* cited by examiner

600

800

US 9,060,714 B2

SYSTEM FOR DETECTION OF BODY MOTION

CLAIM OF PRIORITY

This application claims priority from U.S. Provisional Patent Application Ser. No. 61/119,861, entitled SYSTEM FOR DETECTION OF BODY MOTION, filed on Dec. 4, 2008, which is hereby incorporated by reference as if set forth in full in this application for all purposes.

ACKNOWLEDGEMENT OF GOVERNMENT SUPPORT

This invention was made with Government support under Office of US Army Research Laboratory Grant No. MURIW911NF06-1-0076. The Government may have certain rights to this invention.

COPYRIGHT DISCLAIMER

A portion of the disclosure recited in the specification contains material which may be subject to copyright protection. Specifically, a functional language such as computer source code, pseudo-code or similar executable or design language may be provided. The copyright owner has no objection to the facsimile reproduction of the specification as filed in the Patent and Trademark Office. Otherwise all copyright rights are reserved.

BACKGROUND

Motion sensors and specialized processing can be used to measure and classify the actions of persons or objects. For example, multiple sensors can be placed at body locations such as wrists, ankles, midsection, etc. By analyzing the motion measured by each sensor the subject's overall body movement or action can be determined.

Some sensor-based action recognition approaches utilize a single sensor while others use multiple sensors mounted in different locations to improve the accuracy of overall action recognition. Action recognition systems typically include feature extraction and classification processing that can be either distributed or centralized. However, conventional approaches may not have sufficient accuracy in recognizing the actions of a body or object for many modern applications.

Human action detection is useful in many applications such as medical-care monitoring, athlete training, teleimmersion, human-computer interaction, virtual reality, motion capture, etc. In some applications, such as medical care monitoring that takes place in a user's home, it may be desirable to maintain a low-cost system with a minimal number of sensors, and to reduce resource use such as processing power, bandwidth, cost, etc., while still maintaining desired accuracy and performance.

BRIEF DESCRIPTION OF THE DRAWING(S)

DETAILED DESCRIPTION OF EMBODIMENTS OF THE INVENTION

Figure 1:
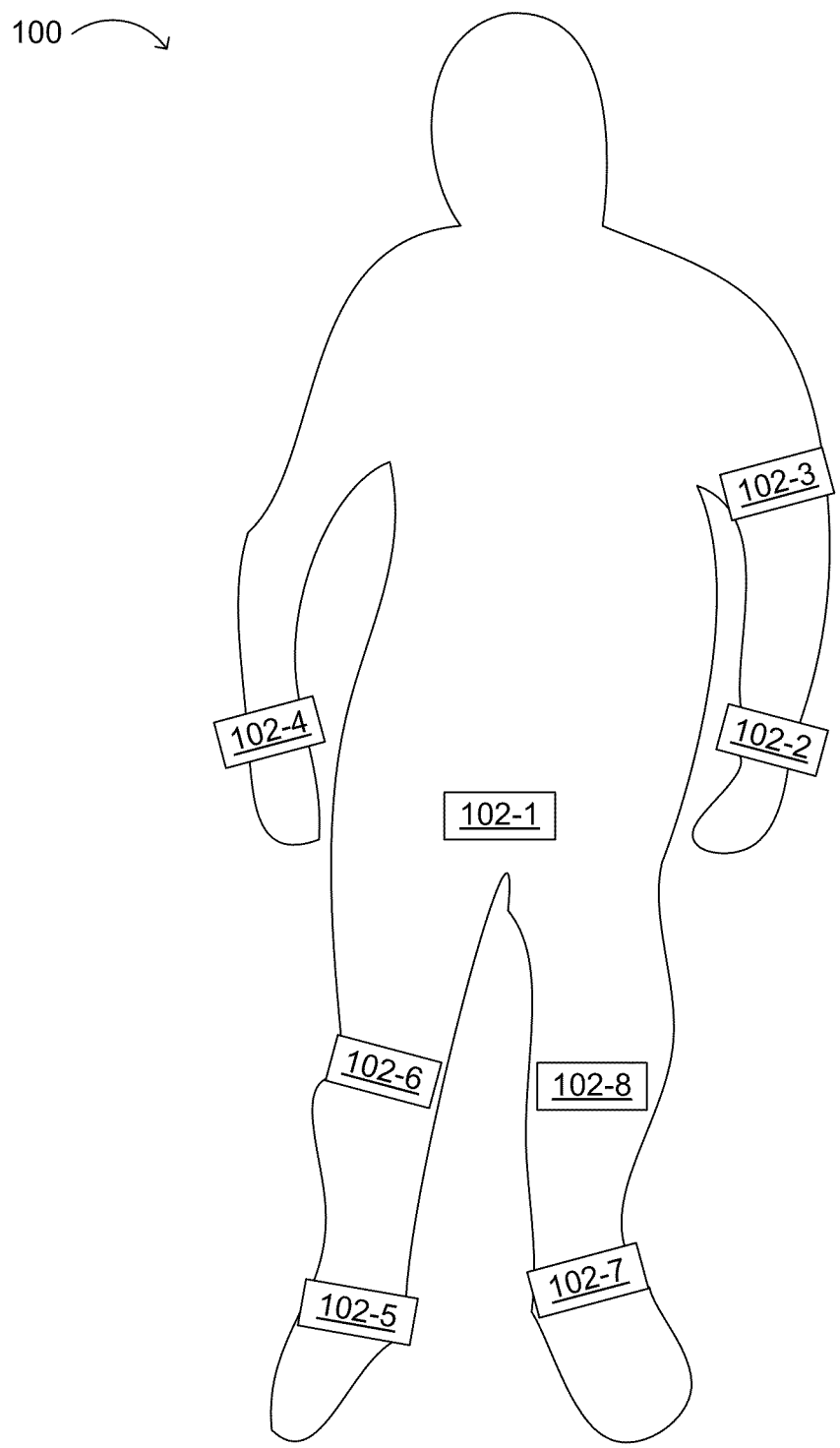
FIG. 1 illustrates an example wireless body sensor arrangement.

In particular embodiments, body motions are determined by using one or more distributed sensors or sensor nodes. Although a preferred embodiment of the invention uses accelerometer and global positioning system (GPS) position sensors, features described herein may be adaptable for use with any other suitable types of sensors or position sensing systems such as, triangulation or point-of-reference sensors (e.g., infrared, ultrasound, radio-frequency, etc.), imaging (e.g., video image recognition), mechanical sensing (e.g., joint extension, shaft encoders, linear displacement, etc.), magnetometers or any other type of suitable sensors or sensing apparatus. Sensors may be included with other functionality such as in a cell phone or other electronic device. In general, various modifications, substitutions or other variations from the particular embodiments described herein will be acceptable and are included within the scope of the claims.

In one embodiment of the present invention, a body action recognition system functions on a single cell phone device, such as Apple iPhone®, GOOGLE gPhone™, Nokia N800/900™, etc. Other mobile devices that include motion sensors can also be employed, such as PDA's, personal navigation systems, etc. While some functionality is possible with standard cell phones, smart phones typically include integrated motion sensors, a processor and memory. These components can be sufficient to support an implementation of the body action recognition algorithm. Particular embodiments may be able to employ whatever capacity a particular cell phone device happens to be equipped with to make an evaluation of the owner's physical movements. For example, ranging location can be provided by cell towers, WiFi locations, GPS sensors, etc.

Magnetometers providing magnetic North indication can be employed by the present invention, as well as a gyroscope and other position sensors. Wireless links which provide useful input to the present invention can include Bluetooth, ZigBee™, etc. The cell phone can be placed at a specified body position such as around the waist or the neck. The software reads motion sensor data directly from the onboard sensor, and executes a classification algorithm via the processor. Information on the statistics or nature of the action classification can be visually or audibly presented on the device to indicate to the user activity level, warnings of dangerous situations (e.g., unsteady gait), health status or other information that can be derived from the action recognition.

In addition, a wireless connection between the cell phone and a base station computer can be established to transmit and store classification results. When potentially harmful human actions are detected (e.g., a fall), alert information (e.g., nature of alert, location, verbal requests) can be transmitted to the monitoring station that can be subsequently forwarded to emergency responders, preferred personal contacts, health care personnel or other preferred contacts. During an alert event, continuous sensor data can be transmitted to a base station that has a more powerful processing capability (more powerful processor and access to a larger human actions database) to validate the human action classification and reduce false alerts.

In one embodiment, sensors are worn on a user's body. Each sensor's data is relayed to a local, in-home, base station and then to a remote managing facility. Preliminary processing can be performed at one or more points in the transfer or relay of sensor data. For example, sensor data can be subjected to sensor-level processing by associating one or more of the sensors with resources such as a digital processor, memory, etc. In one approach, one or more sensors are included in a sensor node assembly (when highly miniaturized may be referred to as a "mote") that can include processing resources and data communication resources such as a wireless transceiver. A body-level controller that includes functions such as a wireless transceiver, cell phone, personal digital assistant (PDA), GPS unit or other customized unit or device worn on the body can also perform preliminary processing in addition to, or in place of, the sensor level processing. A local base station can receive the sensor data and perform additional processing. The local sensor data is transferred to the remote managing facility where further processing and analysis can be performed to make a final determination of body motion or actions based on the sensor data.

In one embodiment, the preliminary processing at the sensor, body or local levels acts to analyze and filter data that is not deemed to be of substantial significance in the ultimate determination of a body motion or action. Other actions can be performed by preliminary processing such as optimizing, calibrating (e.g., normalizing) or otherwise adjusting the raw sensor data in order to aid in efficient motion analysis. Sensor data may be combined or transferred at the sensor, body, local or other lower levels in order to facilitate analysis.

In a preferred embodiment feature extraction and classification functions can be performed at various levels (e.g., local or global) in the system in order to reduce communication bandwidth requirements and sensor node power consumption. In the preferred embodiment a common classification approach can be used at the local and global level simplifying system design while also improving classification accuracy. By modeling the distribution of multiple classes as a mixture subspace model, i.e., one subspace for each action class, we seek the sparest linear representation of the sample with respect to all the training examples. In this model the dominant coefficients in the sparse representation correspond to the class of the test sample. If the action cannot be classified locally the action can be transmitted to a global classifier that uses the same structure but incorporates additional sensor samples to improve classification accuracy. This method is scalable, i.e., multiple classification levels can be used, robust from the viewpoint that the processing structure does change when sensors are added or removed, while at the same time it minimizes communication requirements.

Figure 19:
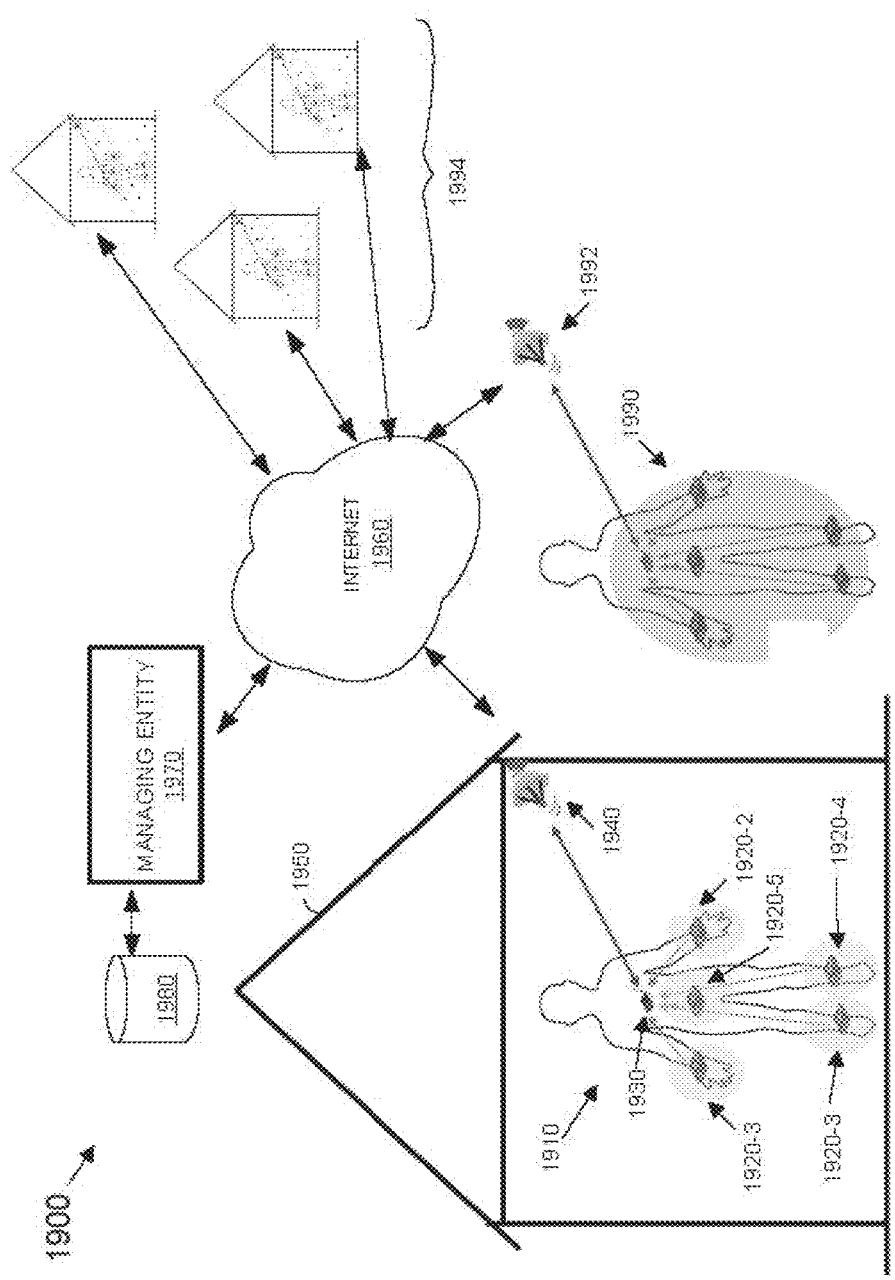
FIG. 19 illustrates basic components and subsystems in a basic description of a system suitable for practicing the invention.

FIG. 19 illustrates basic parts of a system for performing body motion identification according to embodiments of the invention. In FIG. 19, system 1900 includes body sensors 1920 worn by user 1910. In this example, there are five sensors located on the right and left wrists as 1920-1 and 1920-2, respectively; right and left ankles as 1920-3 and 1920-4, respectively, and midsection 1920-5. The sensors are coupled to a central body controller 1930. Data relay between the sensors and central body controller can be by wired or wireless communication. If desired, one or more sensors can be coupled to additional sensor resources such as by using node assemblies to provide data processing or other functions. Similarly, data transfers between the central body controller and the local base station can be by wireless communications such as Bluetooth, Zigbee, Wi-Fi, or the like. Note that, in general, any suitable type of communication link may be used among any one or more components in the system.

Central controller 1930 relays the information to an access point or local base station 1940 that is located in or near to the house or other enclosure 1950. A data link between the local base station is provided via Internet 1960 to managing entity 1970. Managing entity 1970 uses the received sensor data and database 1980 in order to make a determination of an action performed by user 1910. Managing entity 1970 can also send data to the local subsystems such as the local base station, central body controller, sensors, motes, discussed above, in order to control, interrogate or perform other functions with the subsystems.

Managing entity 1970 can interface with many different local subsystems such as outdoor user 1990 having a similar set of sensors as those described above for user 1910. Outdoor user 1990's sensor data is provided to an outdoor base station 1992. Outdoor base station can be, for example, a cellular network site, satellite in a satellite telephone network, radio-frequency communication, etc. Many such indoor and outdoor users can be managed by a single managing entity as illustrated by multiple users at 1994. Although specific numbers and types of components are illustrated, it should be apparent that many variations in type and number are possible to achieve the functionality described herein.

In one embodiment, managing entity 1970 can provide communications to user 1910 via a display and user input device (a "user interface"). For example, the central body controller can be a cell phone having a display, pointing device, touch screen, numeric keypad, QWERTY keyboard, etc. Other devices can be used to provide a user interface such as a desktop personal computer, laptop, sub-notebook, ultra-portable computing device, etc. (not shown).

As described herein (i.e., in this specification and in the included documents), preliminary processing may be performed at any of the local subsystems or at other locations prior to the data reaching managing entity 1970 in order to reduce the amount of data that is relayed downstream. For example, data filtering (i.e., discarding) can occur at low levels in the system such as at the sensor, sensor node, central body controller or other local level of operation. In a preferred embodiment, the computational approach described herein allows functions such as feature extraction and classification to be used to identify false data and "outlier" data. Where false data is data that is not desirable for action classification and wherein outlier data is data that results in a motion classification that is not a motion that is of interest to the system. For example, if the only classifications that are desired to be detected are standing, sitting and walking, then data that results in a determination of a running motion is outlier data. The false data and outlier data can be prevented from further propagation and use in the system by performing local preliminary processing. This improves the efficiency of data processing and can reduce data communication bandwidth requirements and power consumption.

The use of some or all of the functionality described herein allows the system to adapt to changes in the deletion, addition or modification of sensors and sensor data. For example, the Adaptive Global Recognition that uses Distributed Sparsity Classifier (DSC) functions (portions of which may operate at any point in the system) allows the system to continue to perform effectively when a sensor is turned off, removed, malfunctioning, broken or otherwise is halted or impaired in its operation. In some cases, as described herein, performance may actually improve after a sensor is removed or shut off.

Thus, one benefit of the system is that a user can modify the sensor arrangement and the system can automatically adjust to perform with the new arrangement. For example, if a user develops a skin irritation where a sensor is mounted and removes the sensor the system can adapt to the new configuration and still maintain motion identification. In this case, once the managing entity determines that a sensor is missing it can send a message to the user to inform the user of the missing sensor data. The user can then reply to indicate that the user intended that the system be modified by removing a sensor or the user may be alerted that a sensor has stopped without the user's intent.

This type of sensor placement or operation modification in the field is a benefit to ongoing work with the system. "Hot plugging/unplugging" of sensors can be performed where a sensor is added or removed without having to power down other parts of the system or require user modification of system software. Since the managing entity can detect such changes (while still maintaining operations in view of the changes) the managing entity can then communicate with the user to make sure that the changes were intended and the results after the changes are acceptable. Another feature allows the managing entity to turn each sensor on or off remotely in order to test system adaptability before a change is made.

In one embodiment, one or more sensors are coupled to a body, where each sensor is positioned at about a designated location on the body, and where each sensor is configured to acquire motion data related to movement of the designated location on the body and at which the sensor is positioned, and to reduce the motion data into compressed and transmittable motion data; and a base station configured to receive the compressed motion data via wireless communication from at least one of the plurality of sensors, the base station being further configured to remove outlier information from the received motion data, and to match the received motion data to a predetermined action, where the predetermined action indicates a movement of the body.

In one embodiment, a method can include: acquiring motion data related to movement of a designated location on a body using a sensor; reducing the motion data into compressed motion data; transmitting the compressed motion data to a base station using a wireless connection (the base station may be integrated into the sensor as a single module); removing outlier information from the transmitted motion data to create outlier rejected motion data; and matching the outlier rejected motion data to a predetermined action for indicating a movement of the body.

A distributed recognition approach for classification of movement actions using an attachable motion sensing and processing network is described herein. For example, the motion sensor network can be attached to, or wearable by, a human being, and the sensor network can be relatively low-bandwidth (e.g., in a range of about 250 kbit per second at 2.4 GHz for the IEEE 802.15.4 protocol). A set of pre-segmented motion sequences may be utilized as training examples, and an algorithm can substantially simultaneously segment and classify such human actions. Further, particular embodiments can also reject outlying actions that may not be found in the training set.

The classification in particular embodiments can be operated in a distributed fashion using individual sensors on a body, and a base station processing system that is located on the body or remote from the body under detection. In the particular embodiment, the distribution of multiple action classes satisfies a mixture subspace model, with one subspace for each action class. Given a new test sample, a relatively sparse linear representation of the sample with respect to the training examples can be acquired. In this approach, dominant coefficients in the linear representation may correspond to an action class of the test sample. Thus, membership of the dominant coefficients may be encoded in the linear representation. Further, convex optimization solvers are used to compute such representation via $l^1$-minimization, and have been known to be very efficient in processing high-dimensional data in linear or quadratic algorithm complexity. For example, by using up to 8 body sensors, an algorithm in particular embodiments can achieve state-of-the-art accuracy of about 98.8% on a set of 12 action categories (or with one body sensor, the algorithm can achieve accuracy of approximately 60 to 90%. However, particular embodiments can support a relatively large number of different actions (e.g., 10, 20, etc.). In addition, the recognition precision may decrease gracefully using smaller subsets of sensors, validating distributed framework robustness.

Particular embodiments can also utilize wired or wireless communication between each sensor node and the base station. Further, different subsets of sensors that are available (e.g., due to dropped wireless signals) can be accommodated. Software can be used on each sensor node for local computations, and on a central computer or base station. Feature selection or compression of data obtained from each sensor node can be performed to reduce information. Overall performance in particular embodiments is gained from a combination of sensor accuracy and outlier rejection.

Applications of particular embodiments include: (i) monitoring activities in elderly people, the disabled and the chronically ill (e.g., remote over a network) for nursing homes and hospitals; (ii) hospital emergency room monitoring for nursing coverage; (iii) diagnosis of diseases (e.g., Parkinson's, etc.); (iv) monitoring of prisoners or soldiers (e.g., where sensors are embedded in uniforms), such as via base station monitoring; (v) athletic training, (vi) monitoring patients in clinical drug studies, (vii) monitoring of animal activities and (viii) machine monitoring. Of course, particular embodiments are also amenable to many more applications.

Human Action Recognition Introduction

Human action recognition can be achieved using a distributed wearable motion sensor network. One approach to action recognition is computer vision. As compared with a model-based or appearance-based vision system, various aspects distinguish the body sensor network approach of particular embodiments. In one aspect, the system does not require adding cameras or other sensor instrumentation to the environment. In another aspect, the system has the necessary mobility to support continuous monitoring of a subject during the daily activities of the subject. In another aspect, and with the continuing miniaturization of mobile processors and sensors, it has become possible to manufacture wearable sensor networks that densely cover the human body to record and analyze relatively small movements of the human body (e.g., breathing, spine movements, heart beats, etc.). Such sensor networks can be used in applications, such as medical-care monitoring, athlete training, tele-immersion, and human-computer interaction (e.g., integration of accelerometers in Wii game controllers, smart phones, etc.).

FIG. 1 illustrates an example wireless body sensor arrangement system 100. For example, sensors 102 can be positioned at designated locations on a body, such as sensor 102-1 at a waist location, sensor 102-2 at a left wrist location, sensor 102-3 at a left upper arm location, sensor 102-4 at a right wrist location, sensor 102-5 at a right ankle location, sensor 102-6 at a right knee location, sensor 102-7 at a left ankle location, and sensor 102-8 at a left knee location.

In some sensor networks, the computation performed by the sensor node is fairly simple: (i) extract and filter sensor data and (ii) transmit the data to a microprocessor-based server over a network for processing. In particular embodiments, distributed pattern recognition is employed, whereby each sensor node can classify local information. When the local classification detects a possible object or event, the sensor node can become fully active and transmit the measurement to a centralized server. If wireless interconnection is employed, it is desirable to reduce power consumption because, e.g., the power consumption required to successfully send one byte over a wireless channel is equivalent to executing between $1 \times 10^3$ and $1 \times 10^6$ instructions on an onboard processor. Thus, such sensor networks should reduce communication, while preserving recognition performance. On the server side, a global classifier can receive data from the sensor nodes and further optimize the classification. The global classifier can be more computationally involved than the distributed classifiers, but the global classifier may also adapt to changes of available network sensors due to local measurement error, sensor failure, and communication congestion.

Feature extraction in wearable sensor networks can include three major types of features. The first such feature can involve relatively simple statistics of a signal sequence, such as the max, mean, variance, and energy. The second such feature may be computed using fixed filter banks (e.g., fast Fourier transform (FFT), finite impulse response filters, wavelets, etc.). The third such feature may be based on classical dimensionality reduction techniques (e.g., principal component analysis (PCA), linear discriminant analysis (LDA), etc.).

In terms of classification on the action features, some approaches have used such as thresholding or k-nearest-neighbor (kNN) classifications, due to the simplicity of these algorithms with mobile devices. Other more sophisticated techniques have also been used, such as decision trees and hidden Markov models.

For distributed pattern recognition, distributed speech recognition and distributed expert systems have been used, but for most distributed sensor systems, each local observation from the distributed sensors is biased and insufficient to classify all classes of actions. For example, the sensors placed on a lower-body may not perform well in classification of those actions that mainly involve upper body motions (and vice versa). Consequently, traditional majority-voting type classifiers may not achieve the best performance globally.

Figure 2:
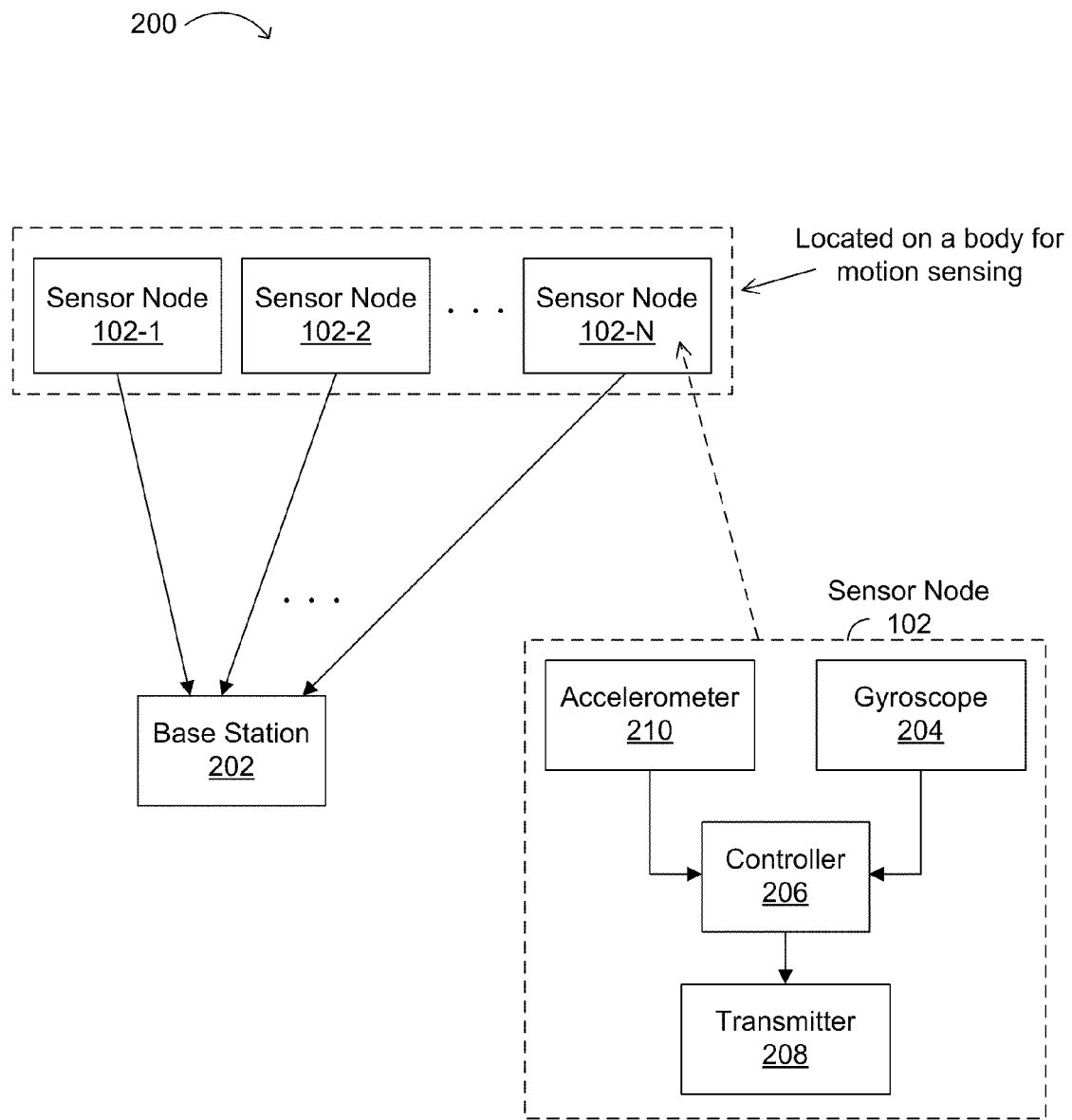
FIG. 2 illustrates an example motion sensor system.

FIG. 2 illustrates an example motion sensor system 200. Any suitable number of sensors 102 (e.g., 102-1, 102-2, ... 102-N) can be located at designated positions on a body for motion sensing. The sensors 102 that are active may then transmit information to base station 202. For example, each sensor 102 can include accelerometer 210 and gyroscope 204. Controller 206 can receive motion data from accelerometer 210 and gyroscope 204, and may provide information to transmitter 208 for transmission to base station 202.

Thus, design of a wearable sensor network in particular embodiments can include: (i) sensors placed at various body locations, which communicate with (ii) a base station that can communicate with a computer server. For example, the base station and computer server can be connected through a universal serial bus (USB) port, or any other suitable connection (e.g., a wireless connection). Further, the sensors and base station may be built using commercially available products such as Tmote Sky™ boards from companies such as Sentilla Corporation of Redwood City, Calif. Such products can run software such as TinyOS on an 8 MHz microcontroller with 10K random-access memory (RAM) and communicates using the 802.15.4 wireless protocol. Each sensor node can include a triaxial accelerometer and a biaxial gyroscope, which may be attached to the Tmote Sky™ board. In this example, each axis is reported as a 12-bit value to the sensor, thus indicating values in the range of +/−2 g for the accelerometer, and +/−500°/s for the gyroscope.

To avoid packet collision in the wireless channel, a time division multiple access (TDMA) protocol can be used to allocate each sensor node a specific time slot during which to transmit data. This allows transmission of sensor data at about 20 Hz with minimal packet loss. To avoid drift in the network, the base station can periodically broadcast a packet to resynchronize individual timers for sensor each node. The code to interface with the sensors and transmit data may be implemented directly on a mote using nesC, a variant of the C programming language. Any other suitable hardware and software approach can be suitable.

In one example, a set of L wearable sensor nodes with triaxial accelerometers and biaxial gyroscopes are attached to the human body. For example, denote $a_1(t)=(x_1(t), y_1(t), z_1(t), \theta_1(t), \rho_1(t))^T \in \Re^5$ as the measurement of the five sensors on node 1 at time t, and $a(t)=(a_1^T(t), a_2^T(t), K, a_L^T(t))^T \in \Re^{5L \cdot 5L}$ collects all sensor measurements. Further, denote $s=(a(1), a(2), K, a(l)) \in \Re^{5Lxl \cdot 5Lxl}$ as an action sequence of length l. Given K different classes of human actions, a set of $n_i$ training examples $\{s_{i,1}, K, s_{I,n_i}\}$ can be collected for each ith class. The durations of the sequences naturally may be different. Given a new test sequence s that may contain multiple actions and possible other outlying actions, a distributed algorithm can be used to substantially simultaneously segment the sequence and classify the actions.

Solving this problem mainly involves challenges of simultaneous segmentation and classification, variation of action durations, identity independence, and distributed recognition. Simultaneous segmentation and recognition from a long motion sequence can be achieved, where the test sequence may contain other unknown actions that are not from the K classes. An algorithm in particular embodiments can be robust as to these outliers.

Figure 3:
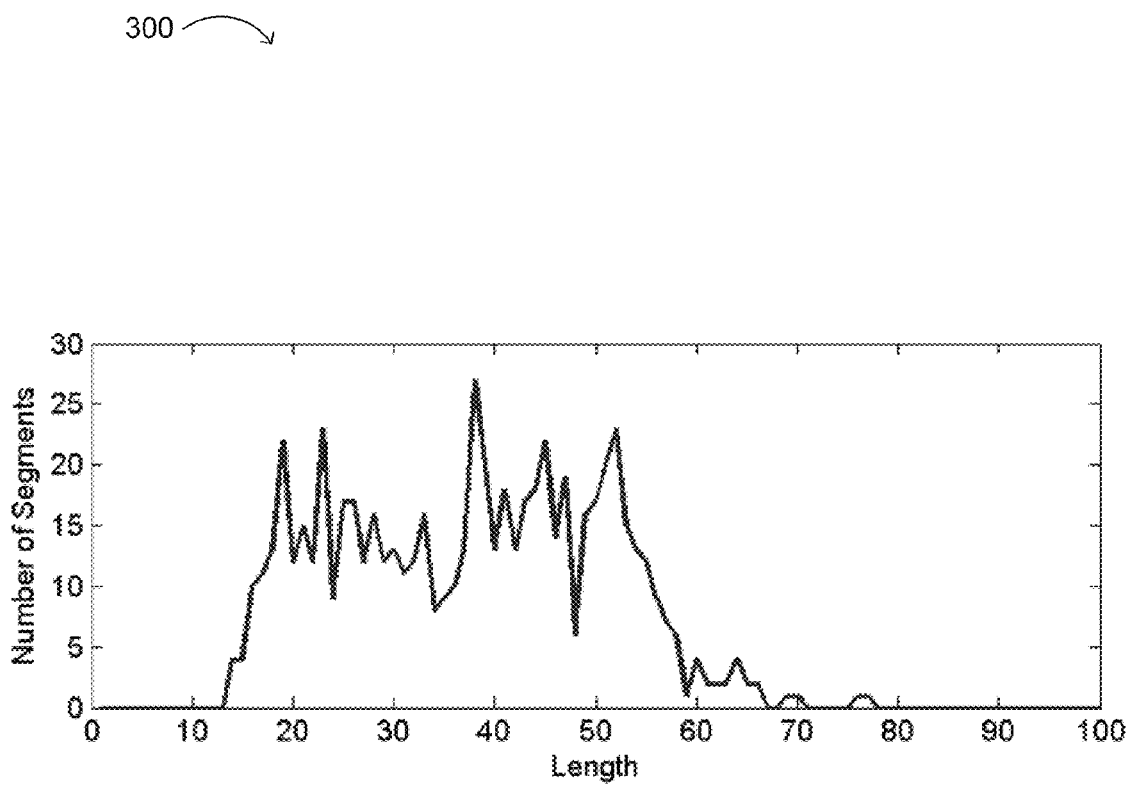
FIG. 3 illustrates an example of action duration variations.

FIG. 3 illustrates an example of action duration variations 300. For variation of action durations, where the durations of different actions can vary dramatically in practice, a difficulty in segmentation of actions may exist in determining duration of a proper action. In addition to the variation of action durations, different people move differently for the same actions, for identity independence.

Figure 4:
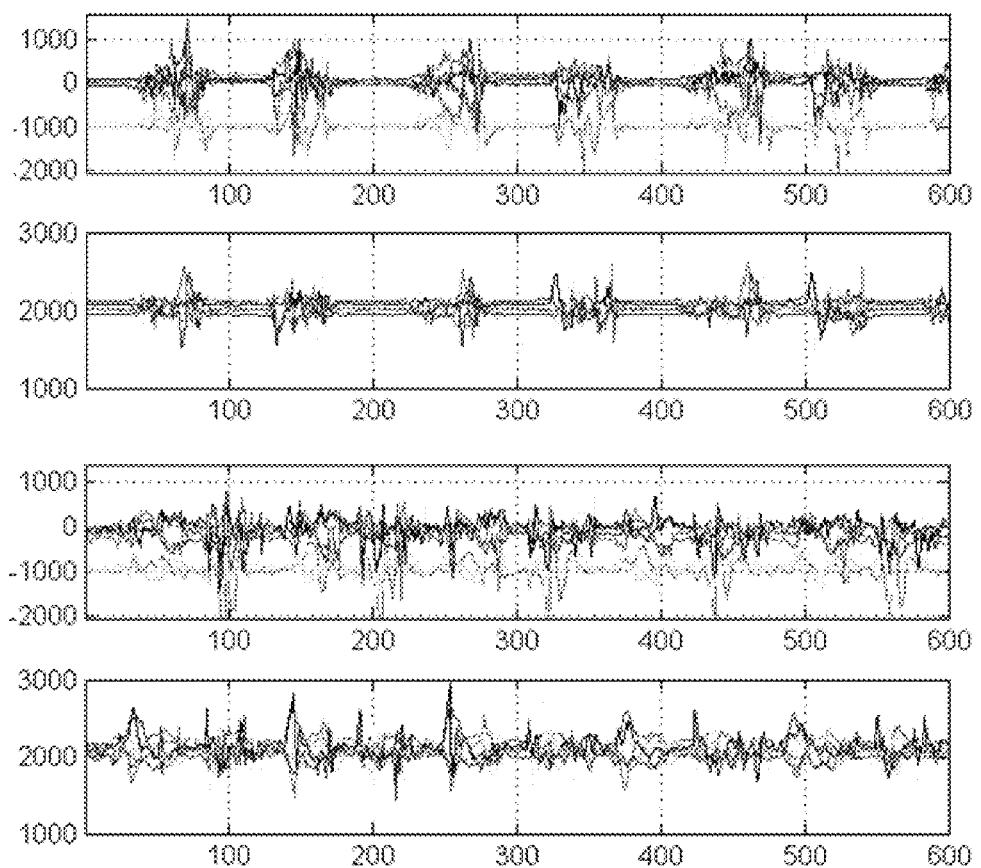
FIG. 4 illustrates example waveforms of accelerometer and gyroscope readings for two repetitive stand-kneel-stand actions.

FIG. 4 illustrates example waveforms 400 of accelerometer and gyroscope readings for two repetitive stand-kneel-stand actions. For a test sequence, identity independent performance can be seen by excluding the training samples of the same subject. FIG. 4 shows readings of x-axis accelerometers (first and third diagrams) and x-axis gyroscopes (second and fourth diagrams) from eight distributed sensors on two repetitive stand-kneel-stand actions or sequences from two subjects.

A distributed recognition system may also consider: (i) how to extract compact and accurate low-dimensional action features for local classification and transmission over a band-limited network; (ii) how to classify the local measurement in real time using low-power processors; and (iii) how to design a classifier to globally optimize the recognition and be adaptive to the change of the network.

In particular embodiments, a distributed action recognition algorithm can simultaneously segment and classify 12 human actions using up to 8 wearable motion sensors. This approach utilizes an emerging theory of compressed sensing and sparse representation, where each action class can satisfy a low-dimensional subspace model. For example, a 10-D linear discriminant analysis (LDA) feature space may suffice to locally represent 12 action subspaces on each node. If a linear representation is sought to represent a valid test sample with respect to all training samples, the dominant coefficients in the sparsest representation correspond to the training samples from the same action class, and hence they encode the membership of the test sample.

In one example system, three integrated components can be employed: (i) a multi-resolution action feature extractor; (ii) fast distributed classifiers via $l^1$-minimization; and (iii) an adaptive global classifier. Particular embodiments can include a method to accurately segment and classify human actions from a continuous motion sequence. The local classifiers that reject potential outliers can reduce the sensor-to-server communication requirements by approximately 50%. Further any subsets of the sensors can be activated or deactivated on-the-fly, due to user control, sensor failure, and/or network congestion. The global classifier may adaptively update the optimization process and improve the overall classification upon available local decision.

Particular embodiments can also support a public database and/or benchmark in order to judge the performance and safeguard the reproducibility of extant algorithms for action recognition using wearable sensors in pattern recognition. For example, a public benchmark system may be referred to as a "Wearable Action Recognition Database" (WARD). Such a database may contain many human or other suitable subjects across multiple age groups, and be made available via the Internet.

Classification via Sparse Representation

Classification via sparse representation can include an efficient action classification method on each sensor node, where action sequences are pre-segmented. Given an action segment of length/from node j, $s_j = (a_j(1), a_j(2), K, a_j(l)) \in \mathfrak{R}^{5 \times l}$, a new vector can be defined:

$$s_j^s \doteq (a_j(1)^T, a_j(2)^T, K, a_j(l)^T)^T \in \mathfrak{R}^{5l},$$ Equation 1 as the stacking of the l columns of $s_j$ (where $s_j$ can be interchangeably used to denote stacked vector $s_j^S$).

Since the length l can vary among different subjects and actions, l can be normalized to be substantially the same for all the training and test samples. For example, this can be achieved by oversampling filtering such as by linear interpolation, FFT interpolation, etc., or by other suitable techniques. After normalization, the dimension of samples sj can be denoted as $D_j = 5l$. Subsequently, a full-body action vector v can be defined that stacks the measurement from all L nodes:

$$v = (s_1^T, s_2^T, K, s_L^T)^T \in \mathfrak{R}^D,$$ Equation 2 where $D = D_1 + K + D_L = 5lL$.

In particular embodiments, the samples v in an action class may satisfy a subspace model, called an action subspace. If the training samples $\{v_1, K, v_{i,m_i}\}$ of the i th class sufficiently span the i th action subspace, given a test sample $y = (y_1^T, K, y_L^T)^T \in \mathfrak{R}^D$ in the same class i, y can be linearly represented using the training examples of the same class:

$$y = \alpha_1 v_1 + K + \alpha_{n_i} v_{n_i} \Leftrightarrow \begin{pmatrix} y_1 \\ y_2 \\ M \\ y_L \end{pmatrix}$$ Equation 3

$$= \left( \begin{pmatrix} s_1 \\ s_2 \\ M \\ s_L \end{pmatrix}_1 \Lambda \begin{pmatrix} s_1 \\ s_2 \\ M \\ s_L \end{pmatrix}_{n_i} \right) \begin{pmatrix} \alpha_1 \\ \alpha_2 \\ M \\ \alpha_{n_i} \end{pmatrix}.$$

Also, such linear constraints may also hold on each node j:

$$y = \alpha_1 s_{j,1} + K + \alpha_{n_i} v_{j,n_i} \in \mathfrak{R}^{D_j}$$

Figure 5:
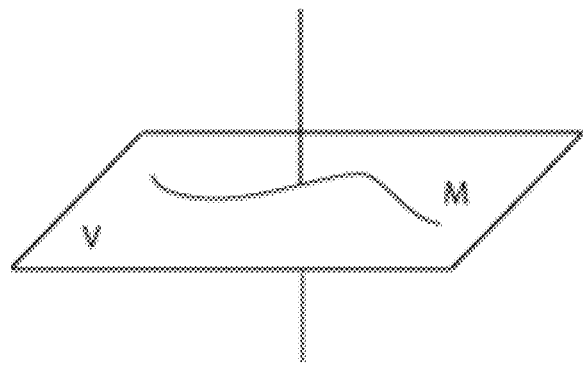
FIG. 5 illustrates an example one-dimensional manifold model using a two-dimensional subspace.

Complex data, such as human actions, typically includes complex nonlinear models. The linear models may be used to approximate such nonlinear structures in a higher-dimensional subspace, as shown in FIG. 5 (e.g., a one-dimensional manifold model 500 using a two-dimensional subspace). Such linear approximation may not produce good estimation of the distance/similarity metric for the samples on the manifold. However, as shown in the example below, given sufficient samples on the manifold as training examples, a new test sample can be accurately represented on the subspace, provided that any two classes do not have similar subspace models.

To recover label(y), one way is to reformulate the recognition using a global sparse representation. Since label(y)=i is unknown, y can be represented using all the training samples from all K classes:

$$y = (A_1 \quad A_2 \quad K \quad A_K) \begin{pmatrix} x_1 \\ x_2 \\ M \\ x_K \end{pmatrix} = Ax,$$ Equation 4 where $A_i = (v_{i,1}, v_{i,2}, K, v_{i,n_i}) \in \mathfrak{R}^{D \times n_i}$ collects the training samples of class i, $x_i = (\alpha_{i,1}, \alpha_{i,2}, K, \alpha_{i,n_i})^T \in \mathfrak{R}^{n_i}$ collects the corresponding coefficients in Equation 3 above, and $A \in \mathfrak{R}^{D \times n}$, where $n = n_1 + n_2 + K + n_K$. Since y satisfies both Equations 3 and 4, one solution of x in Equation 4 can be $x^* = (0, K, 0, x_i^T, 0K, 0)^T$. The solution is naturally relatively sparse, where on average only 1/K terms in $x^*$ are nonzero values.

On each sensor j, solution x* in Equation 4 is also a solution for the representation:

$$y_j = (A_1^{(j)} \ A_2^{(j)} \ K \ A_K^{(j)}) \begin{pmatrix} x_1 \\ x_2 \\ M \\ x_K \end{pmatrix} = A^{(j)}x, \quad \text{Equation 5}$$

where $(A_i^{(j)} \in \Re^{D_j \times n_i}$ includes row vectors in $A_i$ that correspond to the jth node. Hence, x* can be solved either globally using Equation 4, or locally using Equation 5, provided that the action data measured on each sensor node are sufficiently discriminant. Local classification versus global classification will be discussed in more detail below.

As to local classification in each sensor node, one major difficulty in solving Equation 5 is the high dimensionality of the action data. In compressed sensing, one reduces the dimension of a linear system by choosing a linear projection $R_j \in \Re^{d \times D_j}$:

$$\tilde{y} = R_j y_j = R_j A^{(j)} x = \tilde{A}^{(j)} x \in \Re^d. \quad \text{Equation 6}$$

For example, these matrices may be computed offline and simply stored on each sensor node, and $R_j$ may not be computed on the sensor node.

After projection $R_j$, the feature dimension d may be much smaller than the number n of all training samples. Therefore, the new linear system of Equation 6 may be underdetermined Numerically, stable solutions exist to uniquely recover sparse solutions x* via $l^1$-minimization:

$$x^* = \arg\min_x \|x\|_1 \text{ subject to } \tilde{y}_j = \tilde{A}^{(j)} x. \quad \text{Equation 7}$$

In one experiment, multiple projection operators were tested, including PCA, LDA, and a random project. This experiment resulted in the finding that 10-D feature spaces using LDA lead to the best recognition in a very low-dimensional space. After the (sparsest) representation x is recovered, the coefficients can be projected onto each action subspaces:

$$\delta_i(x) = (0, K, 0, x_i^T, 0)^T \in \Re^n, i=1, K, K. \quad \text{Equation 8}$$

Finally, the membership of the test sample $y_j$ may be assigned to the class with the smallest residual:

$$\text{label}(y_j) = \arg\min_i \|\tilde{y}_j - \tilde{A}^{(j)} \delta_i(x)\|_2. \quad \text{Equation 9}$$

In one experiment, 12 action categories were designed: (1) stand-to-sit, (2) sit-to-stand, (3) sit-to-lie, (4) lie-to-sit, (5) stand-to-kneel, (6) kneel-to-stand, (7) rotate-right, (8) rotate-left, (9) bend, (10) jump, (11) upstairs, and (12) downstairs. More details on an example experiment setup are shown below.

To implement $l^1$-minimization on a sensor node, suitable fast sparse solvers can be used. In testing a variety of methods, such as (orthogonal) matching pursuit (MP), basis pursuit (BP), LASSO, and a quadratic log-barrier solver, it was found that BP gives a favorable trade-off between speed, noise tolerance, and recognition accuracy.

To demonstrate the accuracy of the BP-based algorithm on each sensor node (see, e.g., FIG. 1 for example sensor node locations on a body), the actions can be manually segmented from a set of long motion sequences from three subjects. In total, there are 626 samples in the data set in this particular example. The 10-D feature selection is via LDA, and the classification may be substantially identity-independent. The accuracy of this example classification on each node over 12 action classes is shown below in Table 1.

Figure 6:
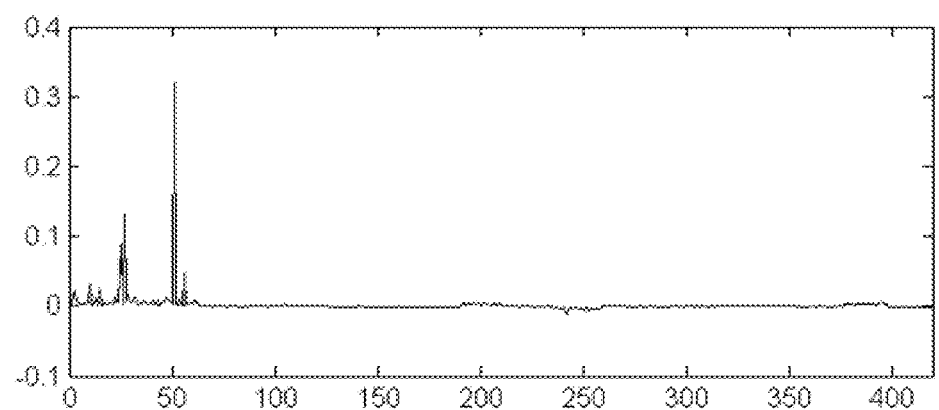
FIG. 6 illustrates an example sparse $l^1$ solution for a stand-to-sit action on a waist sensor with corresponding residuals.
Figure 6:
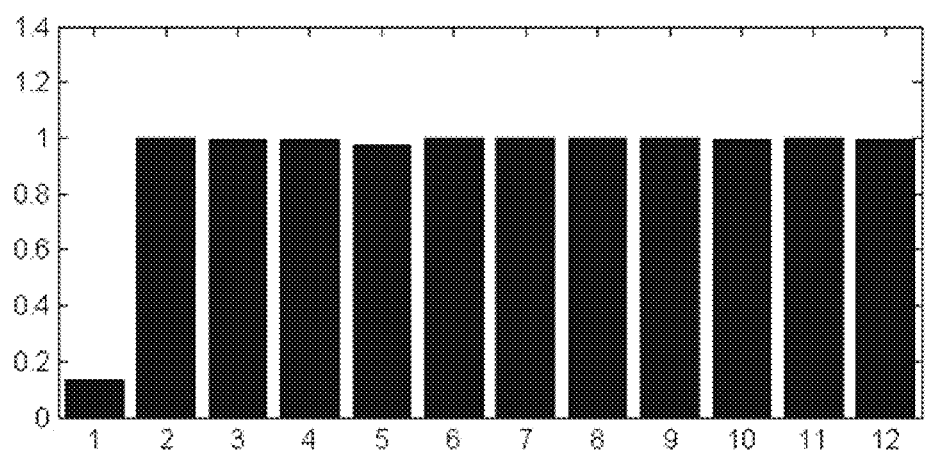

FIG. 6 illustrates an example sparse $l^1$ solution 600 for a stand-to-sit action on a waist sensor node (top diagram), with corresponding residuals (bottom diagram). This represents an example of the estimated sparse coefficients x and its residuals. As an example of the speed involved, a simulation in MATLAB takes an average 0.03s to process one test sample on a typical 3G Hz personal computer (PC). This example shows that if the segmentation of the actions is known, and with no other invalid samples the sensors can recognize the 12 actions individually with relatively high accuracy. Thus, the mixture subspace model is a good approximation of the action data. The sparse representation framework can provide a unified solution for recognizing and segmenting valid actions, while rejecting invalid actions. Further, this approach is adaptive to the change of available sensors on the fly.

Distributed Segmentation and Recognition

Figure 7:
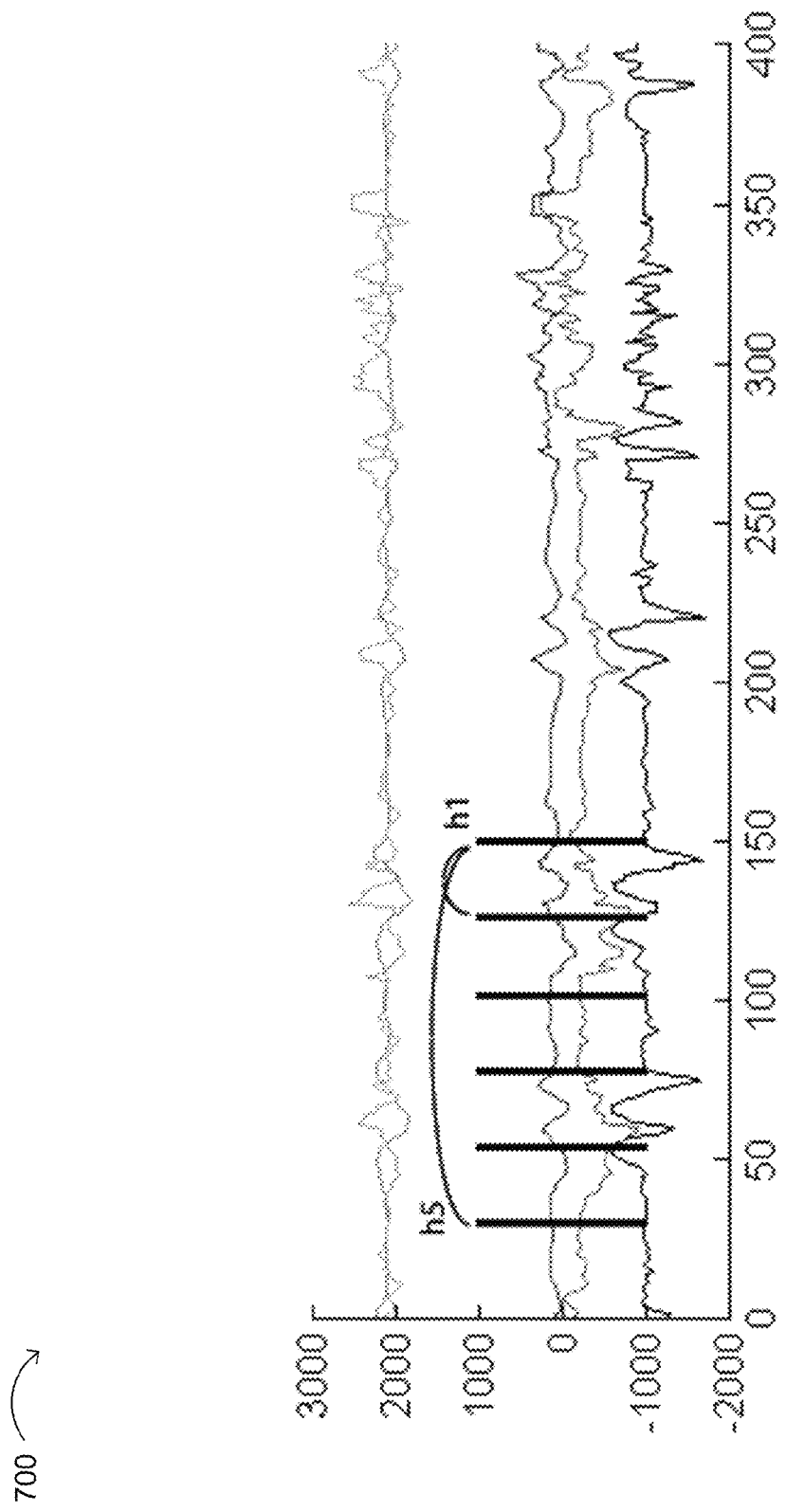
FIG. 7 illustrates example waveforms for a multiple segmentation hypothesis on a wrist sensor node.

A multi-resolution action segmentation can be introduced on each sensor node, and an estimate of a range of possible lengths for all actions of interest can be obtained from the training examples. This estimated range can be evenly divided into multiple length hypotheses: $(h_1, \ldots, h_s)$. At each time t in a motion sequence, the node tests a set of s possible segmentations: $y(1) = (a(t - h_1), \ldots, a(t)), \ldots y(s) = (a(t - h_s), \ldots, a(t))$, as shown in FIG. 7. FIG. 7 illustrates example waveforms 700 for a multiple segmentation hypotheses on a wrist sensor node at a given time (or number of samples on the time domain) t=150 of a "downstairs" sequence. A good segment is $h_1$, while others are false segments, and the movement between about t=250 and about t=350 represents an outlying action that the subject performed.

With each candidate, y may again be normalized to length 1, and a sparse representation x may be estimated using $l^1$-minimization, as discussed above. Thus, based on this sparsity assumption, if y is not a valid segmentation with respect to the training examples due to either incorrect t or h, or the real action performed is not in the training classes, the dominant coefficients of its sparsest representation x may not correspond to any single class. As shown below in Equation 10, a sparsity concentration index (SCI) can be used:

$$SCI(x) \triangleq \frac{K \cdot \max_{j=1, K, K} \|\delta_j(x)\|_1 / \|x\|_1 - 1}{K - 1} \in [0, 1]. \quad \text{Equation 10}$$

Figure 8:
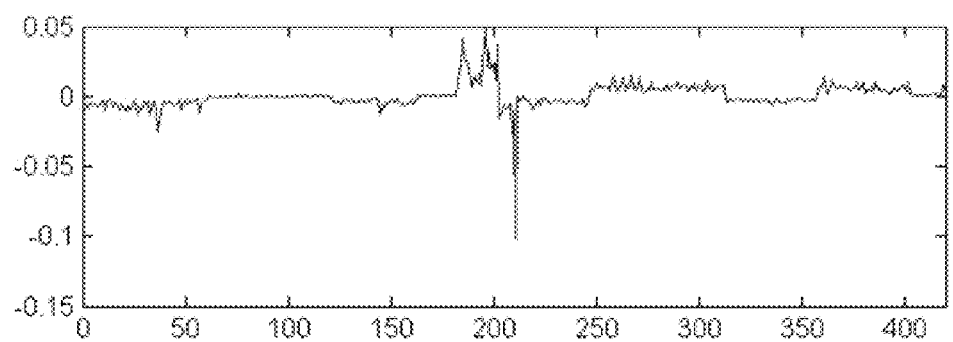
FIG. 8 illustrates an example invalid representation waveform.

If the nonzero coefficients of x are evenly distributed among K classes, then SCI(x)=0, while if all the nonzero coefficients are associated with a single class, then SCI(x)=1. Therefore, a sparsity threshold $\tau_1$ may be introduced and applied to all sensor nodes, where if $SCI(x) > \tau_1$, the segment is a valid local measurement, and its 10-D LDA features $\tilde{y}$ can be sent to the base station. FIG. 8 illustrates an example invalid representation waveform 800, where SCI(x)=0.13. In FIG. 6 above, the action is correctly classified as "Class 1," where SCI(x)=0.7.

A global classifier that adaptively optimizes the overall segmentation and classification can also be introduced. For example, suppose at time t, and with a length hypothesis h, the base station receives L' action features from the active sensors (L'≤L). For example, these features may be from the first L' sensors: $\tilde{y}' = (\tilde{y}_1^T, K, \tilde{y}_{L'}^T)^T \in \Re^{10L'}$. Then the global sparse representation x satisfies the following linear system $$\tilde{y}' = \begin{pmatrix} R_1 & K & 0 & K & 0 \\ M & O & M & \Lambda & M \\ 0 & \Lambda & R_{L'} & \Lambda & 0 \end{pmatrix} Ax = R'Ax = \tilde{A}'x, \quad \text{Equation 11}$$

where $R' \in \Re^{dL' \times D}$ may be a new projection matrix that only extracts action features from the first L' nodes. Consequently, an effect of changing active sensors for the global classification may be formulated via global projection matrix During this transformation, data matrix A and sparse representation x may remain unchanged. The linear system of Equation 6 then becomes a special case of Equation 11 when L'=1.

Similar to the outlier rejection criterion on each sensor node in particular embodiments, a global rejection threshold $\tau_2$ can be introduced. If SCI(x)>$\tau_2$ in Equation 11, this is an indication that the most significant coefficients in x are concentrated in a single training class. Hence $\tilde{y}$ may be assigned to that class, and a corresponding length hypothesis h may provide segmentation of the action from the motion sequence.

Thus in particular embodiments, an overall algorithm on the sensor nodes and on the network server may provide a substantially unified solution to segment and classify action segments from a motion sequence using two simple parameters $\tau_1$ and $\tau_2$. Typically, $\tau_1$ may be selected to be less restricted than $\tau_2$ in order to increase a recall rate, because passing certain amounts of a false signal to a global classifier may be rejected by $\tau_2$ when the action features from multiple nodes are jointly considered. The formulation of adaptive classification Equation 11 via a global projection matrix R' and two sparsity constraints $\tau_1$ and $\tau_2$ provides a relatively simple means of rejecting outliers from a network of multiple sensor nodes. This approach compares favorably to other classical methods, such as kNN and decision trees, because these methods need to train multiple thresholds and decision rules when the number L' and the set of available sensors vary in the full-body action vector $\tilde{y}'=(\tilde{y}_1^T, \Lambda, \tilde{y}_L^T)^T$.

Further, a change of active sensor nodes can affect $l^1$-minimization and the classification of the actions. In compressed sensing, the efficacy of $l^1$-minimization in solving for the sparsest solution x in Equation 11 is characterized by an $l^0/l^1$ equivalence relation. An example condition for the equivalence to hold is the k-neighborliness of $\tilde{A}'$. As a special case, it can be shown that if x is the sparsest solution in Equation 11 for L'=L, x may also be a solution for L'<L. Thus, the decrease of L' may lead to sparser solutions of x.

On the other hand, a decrease in available action features may also make $\tilde{y}'$ less discriminant. For example, if a reduction is made to L'=1, and only a wrist sensor node is activated, then the $l^1$-solution x may have nonzero coefficients associated to multiple actions with similar wrist motions, albeit sparser. This is an inherent problem in methods of classifying human actions using a limited number of motion sensors. In theory, if two action subspaces in a low-dimensional feature space have a small subspace distance after the projection, the corresponding sparse representation cannot distinguish the test samples from the two classes. As will be shown below, reducing the available sensors can reduce the discriminant power of the sparse representation in a lower-dimensional space.

Figure 9:
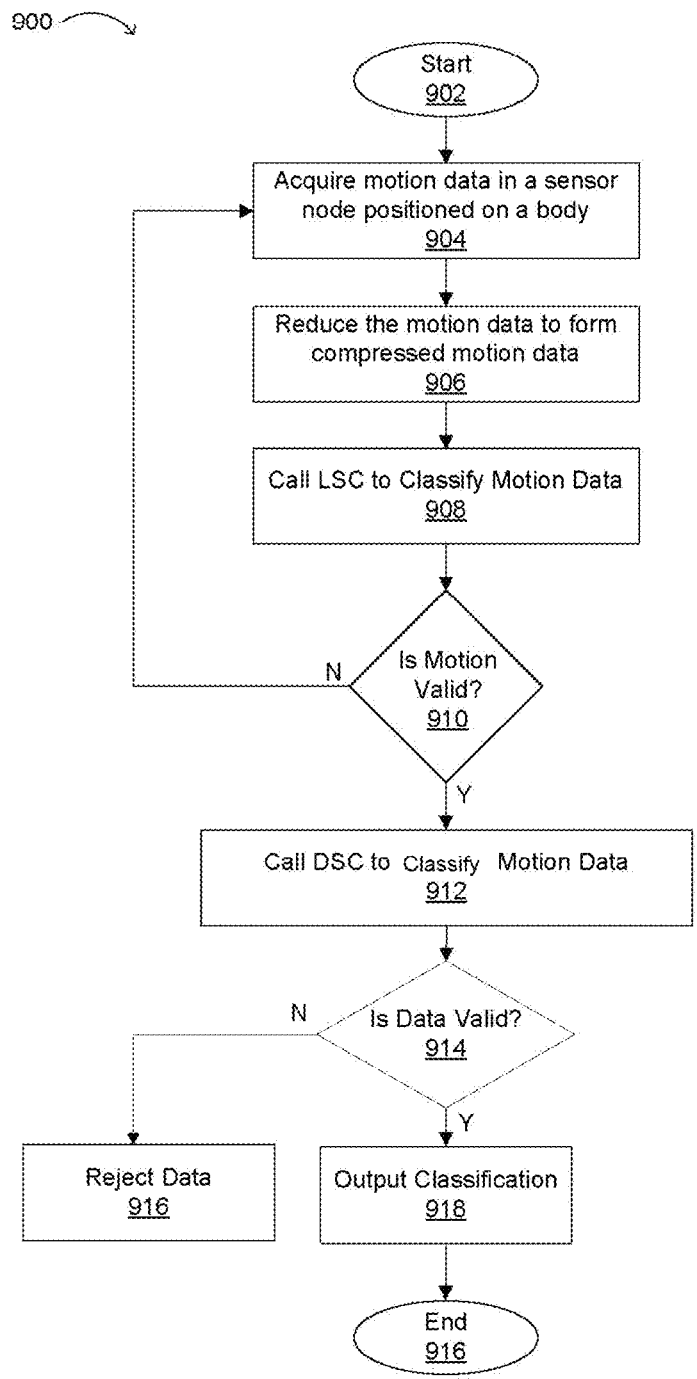
FIG. 9 illustrates a flow diagram of an example method of determining a motion using distributed sensors.

FIG. 9 illustrates a flow diagram of basic steps in an example method 900 of determining a motion using distributed sensors. The flow diagram is entered at (902). Motion data can be acquired in one or more sensors positioned on a body (904). The motion data can then be reduced to form compressed motion data (906). This compressed motion data can then be subjected to LSC classification (908). The steps of 904-906 can be repeated, such as by utilizing TDMA, to receive compressed data from multiple working sensor nodes, or to iteratively receive data from one or more sensor nodes. At step 910 a check is made whether the LSC classification has resulted in a valid motion. If so, step 912 is performed to call the DSC procedure to classify the motion data. If not, sensor data acquisition is resumed.

Outlier information can be removed from the received motion data. Motion data with outlier information removed can then be compared to predetermined actions to indicate movement of the body. At step 914 a check is made as to whether the motion data can be verified as a valid motion. If so, output classification (918) occurs. Otherwise the data is rejected (916), thus completing the flow (916).

Note that the processing of the various steps illustrated in FIG. 9 can be performed at any suitable point in the system of FIG. 19. In one embodiment, (discussed in association with FIG. 19), a managing entity can perform final classification and other functions.

In other embodiments different components in the system can be used to perform various portions of the processing. For example, in a particular embodiment, no managing entity need be present. The managing software can be located within 1930 of FIG. 19, the mobile station per subject. Central body controller 1930 can be used to perform management functions including classification functions such as LSC classification 908 and DSC classification 912. An action database or portions thereof, and other code and data can be stored on different components, e.g., at nodes such as body sensors 1920-1 to 5 and/or 1930 of FIG. 19.

Figure 20:
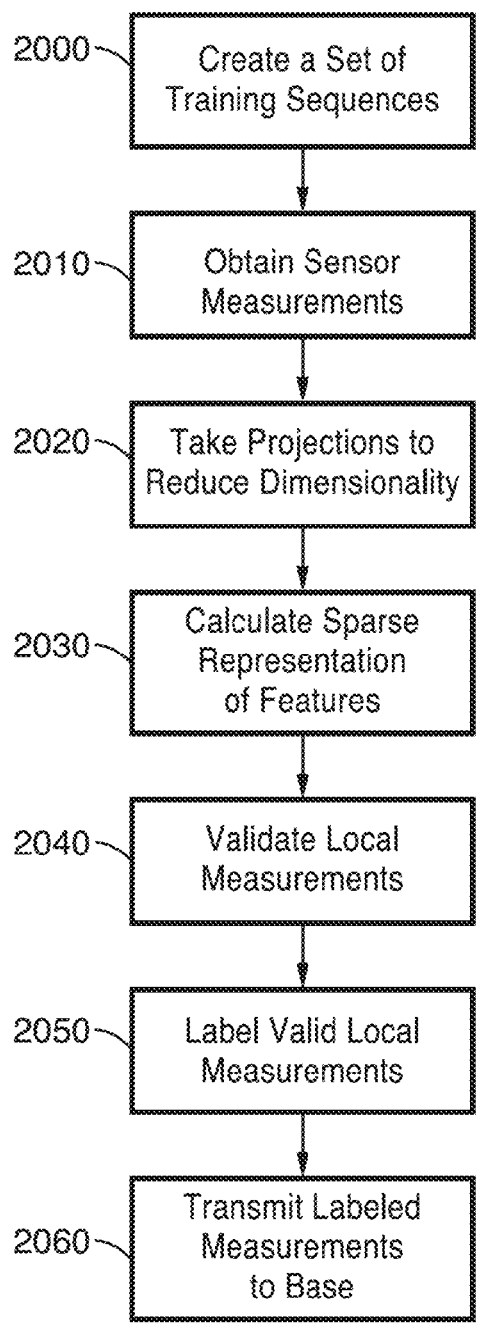
FIG. 20 is a flow diagram of an embodiment of an Local Sparsity Classifier (LSC) system according to the invention.
Figure 21:
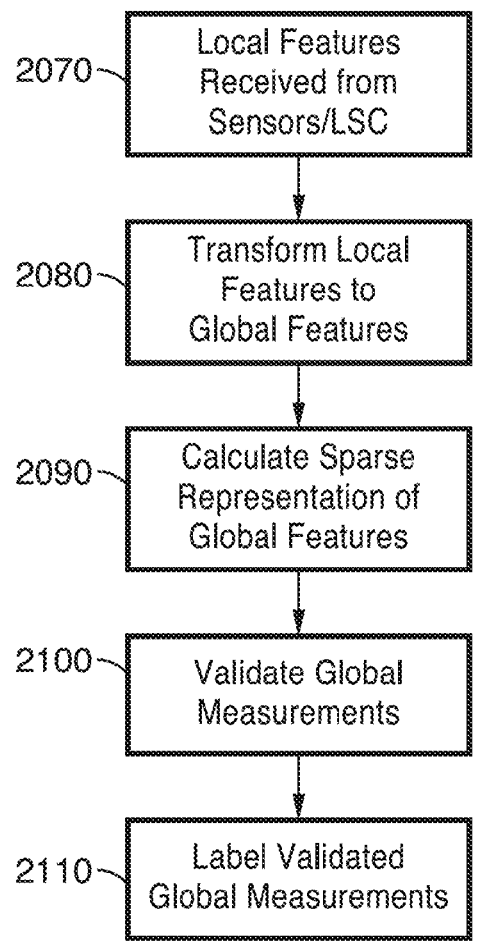
FIG. 21 is a flow diagram of an embodiment of a Distributed Sparsity Classifier (DSC) system according to the invention.

In summary, the classification via sparse representation and distributed segmentation and recognition features of the invention are shown in FIG. 20 and FIG. 21. The preferred embodiment of the limited sparsity classifier (LSC) algorithm functions is shown in FIG. 20. At block 2000, a set of training sequences is provided for each sensor. A training dictionary $A^{(j)}$ and a linear projection matrix $R_j$ pertaining to the i-th sensor are created. The dimensions of the training dictionary $A^{(j)}$ may be reduced using $R_j$: $\{\tilde{A}\}_j = R_j * A_j$.

Measurements from the sensors are received about an event $y_j$ at block 2010 of FIG. 20. Then, at block 2020, a projection $\{\tilde{y}\}_j = R_j Y_j$ is taken to reduce dimensionality.

At block 2030, the sparse representation of feature $\{\tilde{y}\}_i$ based on dictionary $\{\tilde{A}\}_j$ is solved with $x^* = \arg\min_j \|x\|_1$ subject to $\tilde{y}_j = \tilde{A}^{(j)} x$.

Invalid local measurements are identified and eliminated at block 2040 by testing with the sparsity concentration index (SCI) defined by $$SCI(x) \doteq \frac{K \cdot \max_{j=1,K,K} \|\delta_j(x)\|_1 / \|x\|_1 - 1}{K - 1} \in [0, 1].$$

If SCI(x) is less than a threshold, then y is not a valid measurement and the measurement is rejected. However, if SCI(x) is greater than a defined threshold, then y is a valid measurement and the label is recovered.

Labels from valid measurements are recovered at block 2050 with the equation: $\text{label}(y_j) = \arg\min_{i=1,\ldots,K} \|\tilde{y}_j - R_j A^{(j)} \delta_i(x)\|_2$.

Finally, at block 2060, the labeled valid measurement feature $\tilde{y}_j$ is sent to the network base station.

Accordingly, using LSC, a local decision can be made at the sensor level without the need of a base station. The local sensors can make the decision to reject their observations because the classification indicates the measurement cannot possibly be a part of any valid event over the whole network. Likewise, the capability of LSC to directly respond to a local decision without the need of a base station is important for time-critical events. For example, if a sensor is detecting a person falling, it can immediately initiate some predefined response to a potential fall without waiting for observations from other sensors.

Turning now to FIG. 21, the functional steps of the preferred distributed sparsity classifier (DSC) are shown. At block 2070, local features $\tilde{y}_j$ that are sent from a set or subset of active sensors are received at the base station. The number and location of the local features will vary over time on the base station since at each time t, a subset of the sensors will choose to send locally valid measurements to the network and other sensors will not.

The local features are formed into a global feature $\tilde{y}'$ as defined in $\tilde{y}'=(\tilde{y}_1^T, \ldots, \tilde{y}_L^T)^T \in \mathfrak{R}^{dL'}$ at block 2080 of FIG. 21. A global dictionary $\{\tilde{A}\}'$ as determined by Equation 11 can also be compiled.

At block 2090, a sparse representation of the global feature is solved based on the global dictionary $\{\tilde{A}\}'$ with the equation: $x^* = \arg\min \|x\|_1$ subject to $\tilde{y}'=A'x$.

A sparsity concentration index (SCI) is used to prune out invalid local measurements SCI(x) as defined in $$SCI(x) \doteq \frac{K \cdot \max_{j=1,K,K} \|\delta_j(x)\|_1 / \|x\|_1 - 1}{K - 1} \in [0, 1]$$

at block 2100. If the SCI(x) is less than a threshold, then $\{\tilde{y}\}'$ is not a valid measurement and is rejected. If the SCI(x) is greater than a threshold, then $\{\tilde{y}\}'$ is considered to be a valid measurement and the label is recovered.

Finally, at block 2110 of FIG. 21 the label is recovered according to the equation: $\text{label}(\{y\}')=\arg\min_{i=1,\ldots,K}\|\{\tilde{y}\}'-\tilde{A}'\delta_i(x)\|$.

Accordingly, DSC processes a collection of local measurements made available to it over the network by the LSC that have not been rejected by the LSC. DSC is capable of adaptively changing its classification algorithm to produce much better, global classification results. No prior training is necessary to accommodate an arbitrary subset of sensors to deliver their measurements to the DSC.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the methods, a system shown schematically in FIG. 2 and FIG. 19 was assembled. The system included one or more body sensors that had sufficient computing capacity to carry out local sparsity classifier (LSC) calculations. The computing capacity included memory storage of the sensor readings over a period of time, typically a few seconds, and processing units. The distributed sparsity classifier (DSC) was executed when a plurality of sensors aggregate their measurements to a central computer. The central computer was either a stand-alone computer or on one of the body sensors.

The overall algorithm deployed on each sensor node was summarized in the following algorithm, which is called the local sparsity classifier (LSC).

Input: A set of training samples $A^{(j)}=(s_{j,1} \ldots s_{j,n})$, a test sample $y_j$ on a sensor node j, and a linear projection matrix $R_j$.
1: Projection: $\tilde{y}_j = R_j y_j$.
2: $x^* = \arg\min\|x\|_1$ subject to $\tilde{y}_j = R_j A^{(j)} x$.
3: $\text{label}(y_j) = \arg\min_{i=1,\ldots,K} \|\tilde{y}_j - R_j A^{(j)} \delta_i(x)\|_2$.
Output: $\text{label}(y_j)$, action feature $\tilde{y}_j$, and $x^*$.

Accordingly, the LSC algorithm at each sensor j performs two functions with the acquired data in the sensor. First, it uses a linear projection matrix $R_j$ to project the motion measurements ordered in vector form $y_j$ to $\tilde{y}_j$ as $$\tilde{y}_j = R_j y_j.$$

The projection reduces the amount of required memory storage that is necessary to store the measurement data and it further reduces the required power to transmit the measurement data over the network if it is necessary.

Second, LSC attempted to classify $\tilde{y}_j$ as measurements that may represent one of the interested motion classes. The classification is provided by solving a sparse representation of $\tilde{y}_j$ as a linear combination of a prior dictionary $\tilde{A}_j$, whereby columns of $\tilde{A}_j$ store the training examples of known motion measurements that are previously collected at the same sensor location:

$$x^* = \arg\min\|x\|_1 \text{ subject to } \tilde{y}_j = \tilde{A}_j x.$$

Finally, LSC makes decisions about whether the measurements $\tilde{y}_j$ should be transmitted to the central computer to be further processed by DSC. Such a decision has the functionality to significantly reduce the communication power consumption and extends battery life, when the local measurements are deemed not relevant to any of the interested motions and subsequently the measurements are discarded at the sensor node. This technique that utilizes signal processing to reduce the amount of communication is fully suitable for body-worn sensors, as they are highly constrained in terms of the available energy and the battery size.

In this context, the recognition accuracy of LSC on individual nodes was demonstrated based on the wearable action recognition database (WARD) database. The data were sampled from 7 female and 13 male human subjects for a total of 20 subjects with age ranging from 19 to 75. The database includes the following 13 action categories: 1. Stand (ST). 2. Sit (SI). 3. Lie down (LI). 4. Walk for-ward (WF). 5. Walk left-circle (WL). 6. Walk rightcircle (WR). 7. Turn left (TL). 8. Turn right (TR). 9. Go upstairs (UP). 10. Go downstairs (DO). 11. Jog (JO). 12. Jump (JU). 13. Push wheelchair (PU).

For each motion sequence in the WARD database, sample sets of 10 segments of length l in the training set were randomly sampled. In total, there were 20×13×5×10=13,000 training examples produced. During the testing, the LSC process attempted to classify all continuous segments of length l in the WARD database. With respect to each subject, the corresponding training examples were excluded from the training set before classification. It was found that l=45 is a short action duration that yields satisfactory performance, which corresponds to 1.5 seconds given the 30 Hz sampling rate.

The recognition accuracy of LSC was tabulated for all the 13 movement categories. There should be no surprise that LSC alone based on the single node measurement of human actions does not produce good classification, as many human actions engage movements at multiple body parts. For example, nodes at the two ankle positions cannot differentiate walking forward and pushing wheelchair because the feet engage similar movements in both categories. For comparison, performance of a simple global classifier, majority voting, was applied. If all the local decisions are collected and a majority vote is chosen as the overall classification of the test action, LSC achieved 90:2% accuracy. Similarly, nearest neighbor (NN), one of the popular methods used in sensor networks for classification, was applied and tabulated for comparison. The recognition accuracy of NN on the WARD database was observed. Because the inherent correlation between the distributed motion sensors is not considered beyond the majority voting process, the two algorithms generate very similar global recognition accuracy. Using majority voting, nearest neighbor achieves 90:5%.

Example 2

Processing of the sensor node data classified by LSC from all sensors preferably takes place on a central computer configured to receive motion measurement data from all of the LSC modules. The central computer has an adaptive framework for global classification based on all the available distributed sensor data including outlier rejection criterion to identify invalid motion samples measured on the individual sensor nodes. The preferred overall algorithm on the central computer is summarized below is called the distributed sparsity classifier (DSC). DSC provides a unified solution to detect and classify action segments in a network of body sensors using only two simple parameters $\tau_1$ and $\tau_2$.

As described in relation to Equation 10 above, a sparsity concentration index (SCI) is used. If the nonzero coefficients of x are evenly distributed among K classes, then SCI(x)=0; if all the nonzero coefficients are associated with a single class, then SCI(x)=1. Therefore, a sparsity threshold $\tau_1$ is applied on individual sensor nodes. If SCI(x)>$\tau_1$, then the motion sample is considered to be a valid local measurement, and its features $\tilde{y}$ will be sent to the base station computer; otherwise, the sample will be ignored.

In addition, local measurements that are labeled as a valid sample with respect to $\tau_1$ may not truly correspond to a valid human action when multiple sensor data are jointly considered based on the training actions defined in the WARD database. For example, WF, UP, and DO all involve similar upper body movements. On the other hand, if a subject only tries to mimic a WF motion by moving the upper body but not the lower body, the movement becomes an invalid action when both the upper body data and the lower body data are jointly considered. Therefore, a global constraint is used to reject such invalid samples.

Similar to the outlier rejection criterion on each node, a global rejection threshold $\tau_2$ is used. If SCI(x)>$\tau_2$ in the linear system of Equation 11, the most significant coefficients in x are concentrated in a single training class. Hence, $\tilde{y}'$ is assigned to that class. Otherwise, the sample will be rejected as an outlier.

The overall distributed sparsity classifier (DSC) algorithm that is central computer is summarized as follows:
Input: A set of stacked training samples A={$v_1, \ldots, v_n$} from sensors 1, . . . , L, test sample y of action features measured from L active sensors, and sparsity parameters $\tau_1$ and $\tau_2$.
  1: for all each sensor 1≤j≤1 L do
  2: Solve for sparse representation x* using Algorithm of Example 1with parameters $A^{(j)}$ and $y_j$.
  3: If SCI(x*)>$\tau_1$, send feature vector $\tilde{y}_j$ to the network station.
  4: end for
  5: Collect all valid features $\tilde{y}'$, construct corresponding projection matrix R'.
  6: Solve x*=arg min$\|x\|_1$ subject to $\tilde{y}'$=R' Ax.
  7: if SCI(x*)>$\tau_2$ then
  8: label(y)=arg min$_{i=1,\ldots,K}\|\tilde{y}'-R'A\delta_i(x)\|_2$
  9: else
  10: label(y)=−1 (outlier).
  11: end if
Output: label(y).
The functionality of the distributed sparsity classifier (DSC) was with the WARD database and actions described in Example 1 using the DSC algorithm above with five sensor nodes. Action designated 13 in the WARD database, i.e., PU (pushing a wheelchair). While the upper body motion of this action is quite distinct, the lower body motion often resembles several other actions in the database, such as WF and UP.

First, it was observed that the local sparsity classifier (LSC) returned five different labels with respect to the local measurements on the five sensors. It shows that majority-voting type solutions mostly should fail to correctly classify this motion. Second, using a threshold $\tau_1$ against the SCI values of the representations, a certain number of the local motions were rejected as invalid measurements.

For example, if it is assumed that $\tau_1$=0.1 is selected for all five sensors, then measurements from Sensors 1 and 2 were rejected and DSC solves for a sparse representation using the three action features from sensors 3, 4, and 5.

It was observed that at the node level none of Sensors 3-5 correctly classifies the action based on the available local observations, because they are also similar to other actions such as UP, TR, and WR. However, when the measurements from multiple sensors are combined in Equation 11 to represent the full-body motion, the incorrect local decisions are rectified. Such ability is the main reason that the DSC framework can outperform other majority-voting type algorithms.

Example 3

Examination of the performance of the DSC framework using the WARD database was conducted using two different scenarios. First, the classification accuracy with different subsets of motion sensors available in the network was calculated to verify that DSC is adaptive to the change of network configuration on-the-fly due to real-world conditions such as sensor failure, battery failure, and network congestion.

Second, the effect of the local outlier rejection threshold $\tau_1$ to the accuracy of the global classification was considered. Higher rejection thresholds save power consumption in communication at the expense of less local information available to the global classifier, and vice versa. It is important to note that to measure the performance under the identity-independence assumption, all training examples of a test subject should be excluded from the training set during the experiment. For each motion sequence in the WARD database, random samples of 10 segments of length l=45 were used as training examples.

In the first scenario, the performance of DSC was first tested by manually eliminating a certain number of available sensors in the network. Based on the total number L' of the Locality Preserving Projection (LPP) feature vectors that were received, DSC was able to update the classification criterion on-the-fly and adapt to the potentially adversary condition. The performance of the algorithm was quantified by false positive rate (FPR), verification rate (VR), and active sensor rate (ASR) metrics. For all the trials, the outlier rejection threshold parameters $T_1$ and $T_2$ were set to be 0.08, respectively. The duration I of the test action length is set to be 45, which corresponds to 1.5 seconds given the 30 Hz sampling rate. When all continuous action segments of length 45 are classified in the experiment, the total number of test samples amounts to 500828.

In the second scenario, the effect of different local rejection threshold $\tau_1$ values on the global classification was tested. In this case, the global rejection threshold $\tau_2$ was fixed at 0:08. It was observed that naturally the ASR rate decreases as $\tau_1$ increases. For example, compared to ASR=91:85% when $\tau_1$=0:08, the rate was reduced to 45.58% when $\tau_1$=0:18.

Accordingly, on average less than half of the sensors transmitted action features during the evaluation.

With more than half of the sensors inactive in the network to conserve power consumption, it was shown that DSC still achieves below 8% FPR globally, and VR is above 88%. The result corroborates the design principle of the DSC algorithm that the distributed classification framework via sparse representation is capable of effectively reducing the power consumption on communication yet at the same time preserving highly accurate recognition accuracy.

Performance evaluations under these two scenarios demonstrate that a set of 13 action classes can be accurately represented and classified using a set of 40-D LPP features measured at multiple body locations. The distributed algorithm, i.e., distributed sparsity classifier (DSC) framework, provides a unified solution based on $l^1$-minimization to classify valid action segments and reject outlying actions on the sensor nodes and the base station.

Example 4

To further demonstrate the applicability of the system, a cellular phone that incorporated a three axis accelerometer (Apple iPhone®) was utilized as a sensor node for human action classification. A software application was loaded on the iPhone that enabled streaming of three axis accelerometer data via a Wi-Fi (IEEE 802.11 protocol) data link to a PC. Five (5) subjects were studied. Wearing the iPhone attached to a lanyard worn around the neck, subjects performed a series of six action categories: (1) stand-to-sit, (2) sit-to-stand, (3) walk, (4) upstairs, (5) downstairs and (6) stand still. A subset of the accelerometer data collected was hand segmented to create training examples for each human action class. Continuous, non segmented accelerometer data, was processed using LSC and the predicted action class was compared to the known actions recorded during the test. Human action classification accuracy of 86% was achieved using LDA projection of two second data segments.

Example 5

Performance of the system may be validated using a data set collected from, e.g., three male subjects at ages of 28, 30, and 32. In this particular experiment, 8 wearable sensor nodes were placed at different body locations, such as shown in FIG. 1. A set of 12 action classes was designed: (1) Stand-to-Sit (StSi); (2) Sit-to-Stand (SiSt); (3) Sit-to-Lie (SiLi); (4) Lie-to-Sit (LiSi); (5) Stand-to-Kneel (StKn); (6) Kneel-to-Stand (KnSt); (7) Rotate-Right (RoR); (8) Rotate-Left (RoL); (9) Bend; (10) Jump; (11) Upstairs (Up); and (12) Downstairs (Down). This system was tested under various action durations. Toward this end, the subjects were asked to perform StSi, SiSt, SiLi, and LiSi with two different speeds (slow and fast), and to perform RoR and RoL with two different rotation angles (90° and 180°). The subjects were asked to perform a sequence of related actions in each recording session based on their own interpretations of the actions. There are 626 actions performed in the data set (see, e.g., Table 3 below for the numbers in individual classes).

Table 2 below shows precision versus recall of the algorithm with different active sensor nodes. For these particular experiments, $\tau^1=0.2$ and $\tau^2=0.4$. When all sensor nodes are activated, the algorithm can achieve about 98.8% accuracy among the extracted actions, and 94.2% detection of the true actions. The performance may decrease when more sensor nodes become unavailable to the global classifier. Experimental results show that if one sensor node is maintained on the upper body (e.g., sensor 102-2 at position 2 in FIG. 1) and one motion sensor node is maintained on the lower body (e.g., sensor 102-7 at position 7 in FIG. 1), the algorithm can still achieve about 94.4% precision and 82.5% recall. Further, on average the 8 distributed classifiers that reject invalid local measurements reduce the node-to-station communication by about 50%.

As to the relatively low recall on single sensor nodes (e.g., 102-2 and 102-7), this is due to the relatively large number of potential outlying segments presented in a long motion sequence (see, e.g., FIG. 7). Also, the difference may be compared using two "confusion" tables (see, e.g., Tables 3 and 4 below). As shown in these examples, a single node (e.g., 102-2) that is positioned on a left wrist performed poorly mainly on two action categories: Stand-to-Kneel and Upstairs-Downstairs, both of which involve significant movements of the lower body, but not the upper body. This is one reason for the low recall shown in Table 2 above. On the other hand, for the actions that are detected using sensor node 102-2, the system can still achieve about 90% accuracy, thus demonstrating the robustness of the distributed recognition framework.

Examples of classification results are shown to demonstrate algorithm accuracy using all 8 sensor nodes (e.g., 102-1 through 102-8). Each of FIGS. 10-18 plots the readings from x-axis accelerometers on the 8 sensor nodes. The segmentation results are then superimposed. Indications of correctly classified action segment locations, as well as false classification locations are shown, and some valid actions may not be detected by the algorithm.

Figure 10:
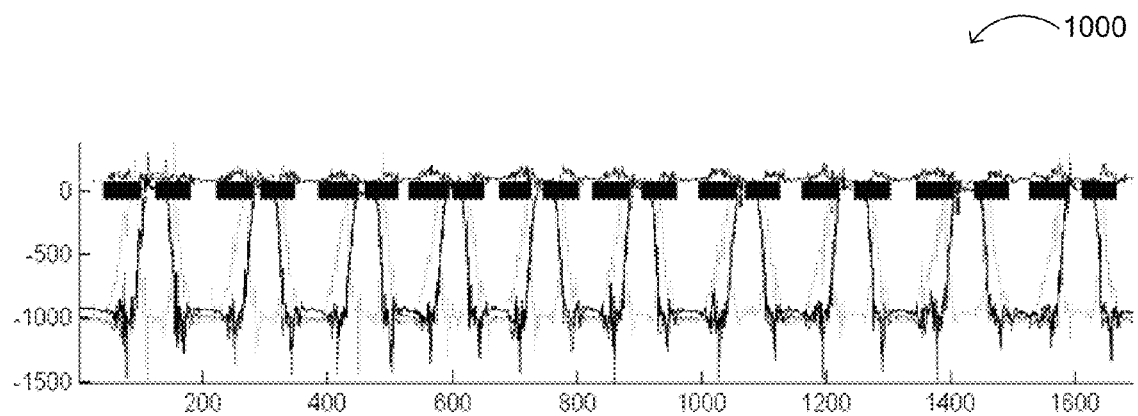
FIG. 10 illustrates example waveforms for an x-axis accelerometer reading for a stand-sit-stand action.
Figure 11:
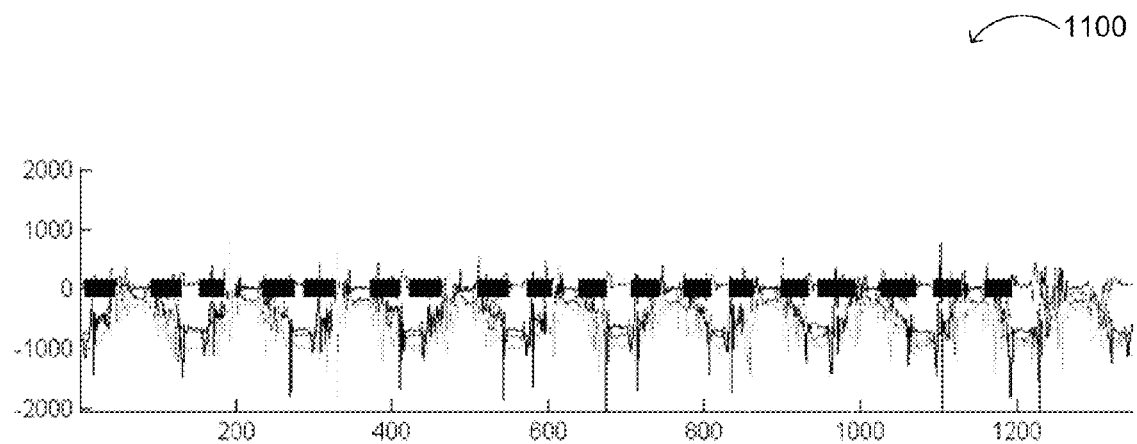
FIG. 11 illustrates example waveforms for an x-axis accelerometer reading for a sit-lie-sit action.
Figure 12:
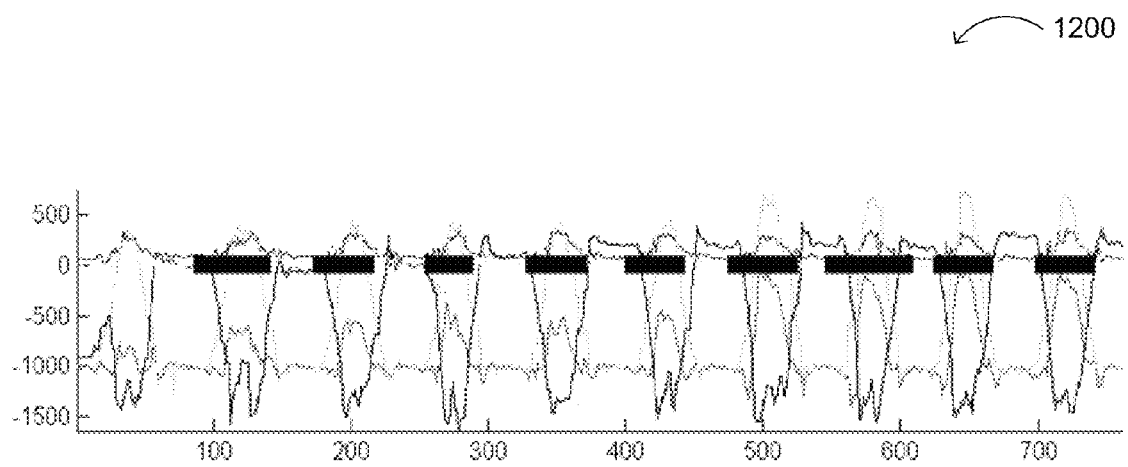
FIG. 12 illustrates example waveforms for an x-axis accelerometer reading for a bend down action.
Figure 13:
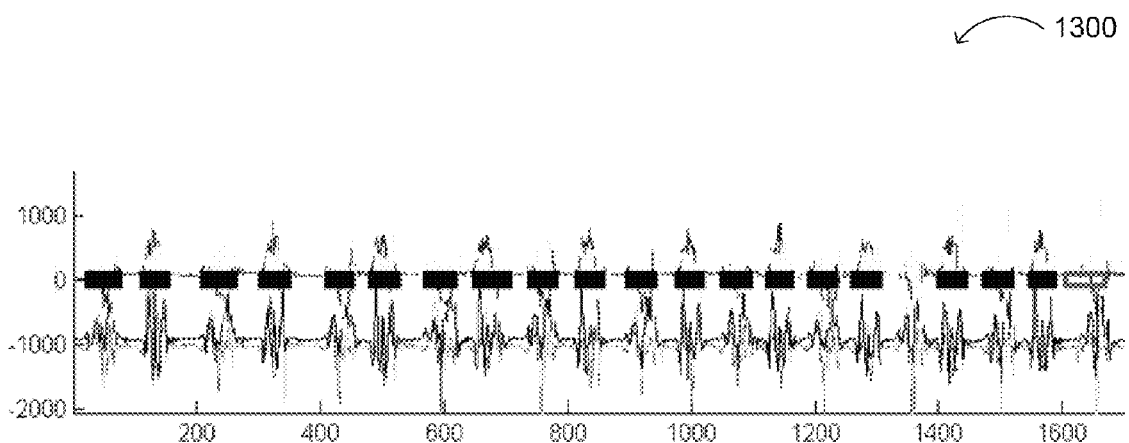
FIG. 13 illustrates example waveforms for an x-axis accelerometer reading for a kneel-stand-kneel action.
Figure 14:
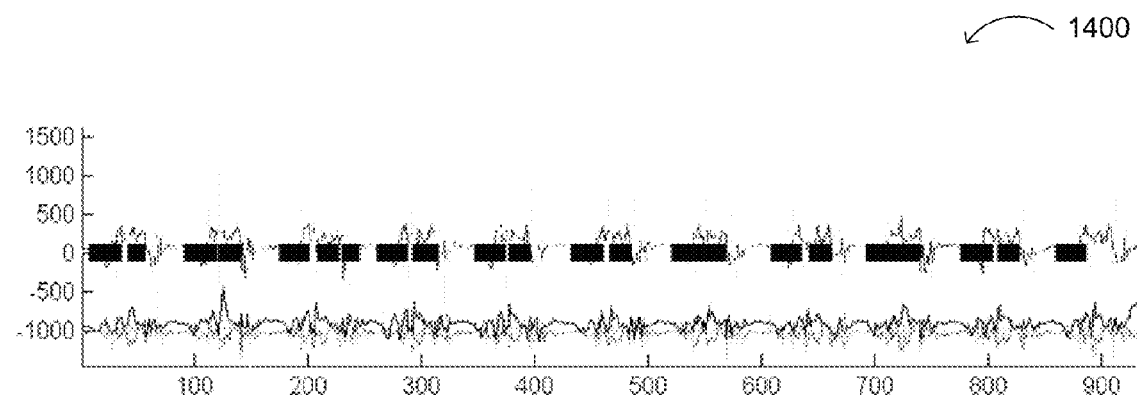
FIG. 14 illustrates example waveforms for an x-axis accelerometer reading for a turn clockwise then counter action.
Figure 15:
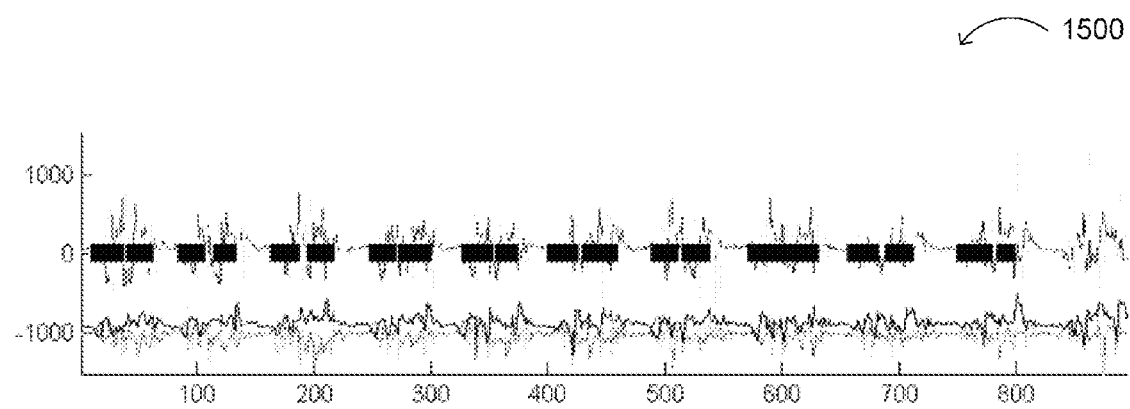
FIG. 15 illustrates example waveforms for an x-axis accelerometer reading for a turn clockwise 360° action.
Figure 16:
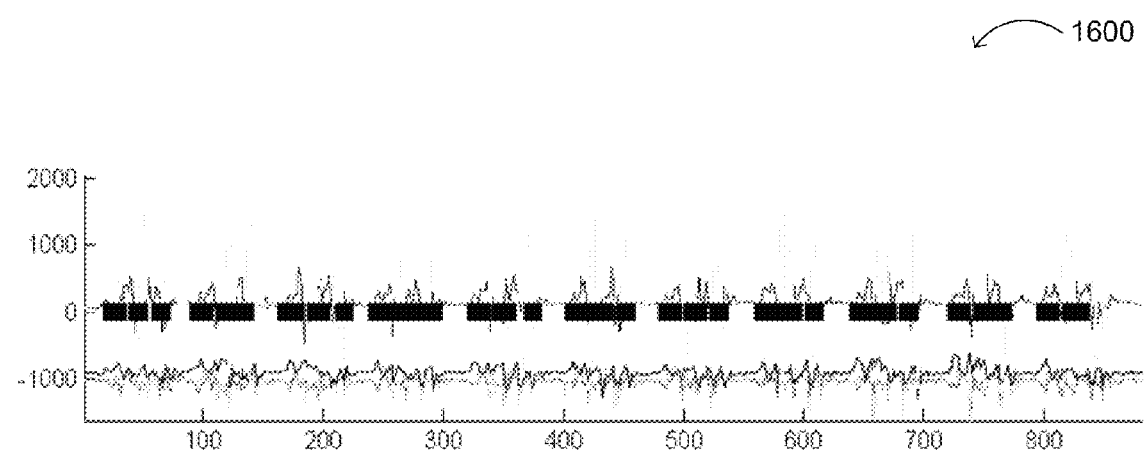
FIG. 16 illustrates example waveforms for an x-axis accelerometer reading for a turn counter clockwise 360° action.
Figure 17:
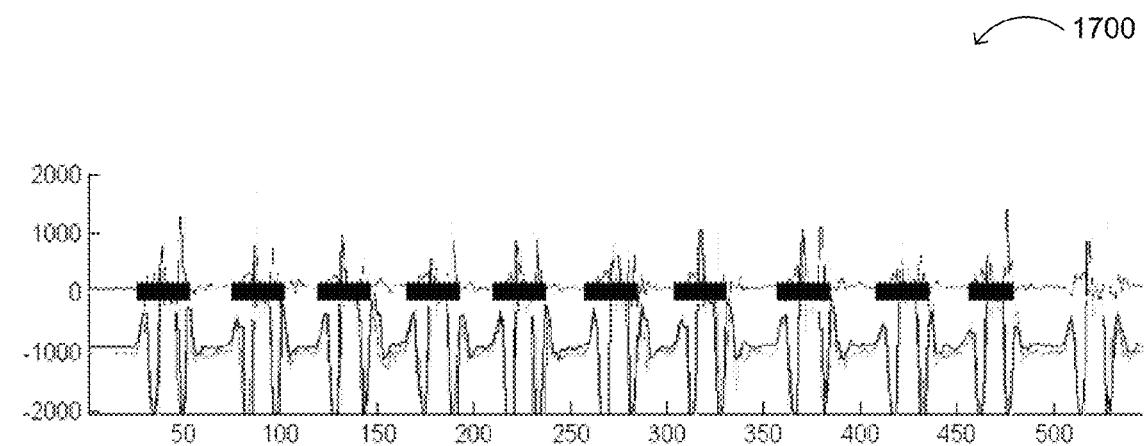
FIG. 17 illustrates example waveforms for an x-axis accelerometer reading for a jump action.
Figure 18:
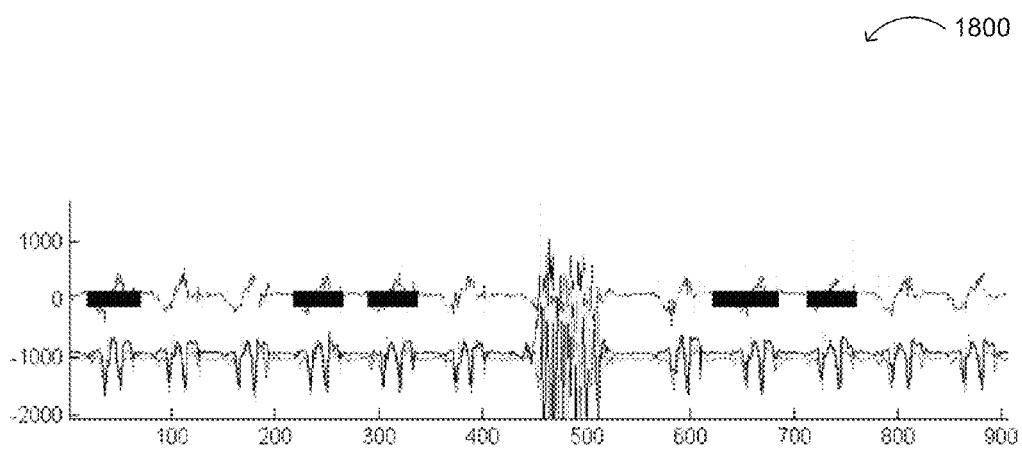
FIG. 18 illustrates example waveforms for an x-axis accelerometer reading for a go upstairs action.

FIG. 10 illustrates example waveforms 1000 for an x-axis accelerometer reading for a stand-sit-stand action. FIG. 11 illustrates example waveforms 1100 for an x-axis accelerometer reading for a sit-lie-sit action. FIG. 12 illustrates example waveforms 1200 for an x-axis accelerometer reading for a bend down action. FIG. 13 illustrates example waveforms 1300 for an x-axis accelerometer reading for a kneel-stand-kneel action. FIG. 14 illustrates example waveforms 1400 for an x-axis accelerometer reading for a turn clockwise then counter action. FIG. 15 illustrates example waveforms 1500 for an x-axis accelerometer reading for a turn clockwise 360° action. FIG. 16 illustrates example waveforms 1600 for an x-axis accelerometer reading for a turn counter clockwise 360° action. FIG. 17 illustrates example waveforms 1700 for an x-axis accelerometer reading for a jump action. FIG. 18 illustrates example waveforms 1800 for an x-axis accelerometer reading for a go upstairs action.

In one experiment, a cellular phone that incorporated a three axis accelerometer (Apple iPhone®) was utilized as a sensor node for human action classification. A software application was loaded on the iPhone that enabled streaming of three axis accelerometer data via a Wi-Fi (IEEE 802.11 protocol) data link to a PC. Five (5) subjects were studied. Wearing the iPhone attached to a lanyard worn around the neck, subjects performed a series of six action categories: (1) stand-to-sit, (2) sit-to-stand, (3) walk, (4) upstairs, (5) downstairs and (6) stand still. A subset of the accelerometer data collected was hand segmented to create training examples for each human action class. Continuous, non segmented accelerometer data, was processed using LSC and the predicted action class was compared to the known actions recorded during the test. Human action classification accuracy of 86% was achieved using LDA projection of two second data segments.

Other applications may benefit from aspects or embodiments of the invention. For example, multiple sensors could be placed at designated positions on manufacturing equipment and by analyzing the data captured by each sensor, the "health" of the production line could be determined. Another example is a power management application where local conditions of power generation, consumption, loss and other factors are monitored and used to adjust the performance of the power system, performing local classification and/or data filtering and aggregation may reduce the amount of data traffic, reduce complexity of analysis, improve speed or efficiency of the system, or provide other benefits. In general, any system that uses distributed data sensing and data relay may benefit from features described herein.

Higher classification accuracy may be realized using features described herein. For example, as shown in the accompanying References, a higher human action classification accuracy may be realized such as in the range 95% to 99% versus 85% to 90% for other approaches. False alarms nay be reduced, which has been a significant problem plaguing other systems.

Power consumption may be reduced by requiring less data transmission between nodes and base station since only outlier classifications require transmission and global consideration. Thus, continuous streaming of data need not be required.

The system accuracy can degrade gracefully with the loss of sensor nodes. The system design is more easily scalable as additional nodes can be added to improve performance or add functionality.

Embodiments described herein can support the expansion or introduction of new training data to help the system to adapt or learn as it is used. This can be important since most previous systems have been "one-size-fits-all" and as a consequence accuracy and false alarms have been an issue.

In one embodiment, the approach requires only two parameters to optimize system performance—outlier threshold at the local classifier and at the global level. Other approaches can require significant tuning to obtain good performance. Embodiments can use the same or similar classifier algorithms at the mote (i.e., node, sensor or body) level and at the global level, simplifying the system development.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art.

Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A method for classifying aggregated data in a distributed sensor system, comprising:
    obtaining sensor data from a plurality of sensors at a local site;
    performing a local classification of the sensor data using local processing, the local processing comprising:
        taking projections of the sensor data to reduce dimensionality;
        calculating sparse representations of features using training sequences;
        validating local measurements;
        classifying valid local measurements; and
    transmitting classified valid measurements to a network base station.

2. The method as recited in claim 1, wherein a projection $\{\tilde{A}\}_j = R_j A_j$ and $\{\tilde{y}\}_j = R_j Y_j$ is taken for each sensor j to reduce dimensionality of the obtained training sensor data and query measurements.

3. The method as recited in claim 1, wherein the sparse representation of measurement feature $\{\tilde{y}\}_j$ based on training dictionary $\{\tilde{A}\}_j$ is solved with $x^* = \mathrm{argmin}_j \|x\|_1$ subject to $\tilde{y}_j = \tilde{A}_j x$.

4. The method as recited in claim 1, wherein the validation of local measurements comprises:
    comparing local measurements to a sparsity concentration index (SCI); and
    validating local measurements that are above an SCI threshold.

5. The method as recited in claim 4, wherein the sparsity concentration index (SCI) is defined by $$SCI(x) \doteq \frac{K \cdot \max_{j=1,K,K} \|\delta_j(x)\|_1 / \|x\|_1 - 1}{K-1} \in [0,1],$$

where K is the number of classes.

6. The method as recited in claim 1, further comprising:
    transmitting labeled valid local measurements from a local processor to a base station receiver.

7. The method as recited in claim 1, further comprising:
aggregating valid local sensor measurements from one or more sensors at a network base station; and
performing a global classification of the aggregated local sensor data, the global classification comprising:
  forming global features from valid local measurements from a plurality of sensors;
  calculating sparse representations of global features;
  validating global features;
  classifying valid global features; and
  labeling global features and their corresponding local features.

8. The method as recited in claim 7, wherein the sparse representation of a global feature is solved based on a global dictionary $\{\tilde{A}\}'$ with the equation: $x^* = \arg\min\|x\|_1$ subject to $\tilde{y}' = A'x$.

9. The method as recited in claim 7, wherein the validation of global features comprises:
  comparing global measurements to a sparsity concentration index (SCI); and
  validating global measurements that are above an SCI threshold.

10. The method as recited in claim 7, wherein the label is recovered according to the equation: label $(\{y\}') = \mathrm{argmin}_{i=1,\ldots,K}\|\{\tilde{y}\}' - \tilde{A}'\delta_i(x)\|$.

11. A method for classifying aggregated data in a distributed sensor system, comprising:
  obtaining sensor data from a plurality of sensors at a local site;
  performing a local classification of the sensor data with local processing, the local processing comprising:
    taking projections of the obtained sensor data to reduce dimensionality;
    calculating sparse representations of measurements using training sequences;
    validating local measurements; and
    labeling valid local measurements;
  transmitting labeled valid local measurements from a local processor to a base station receiver; and
  performing a global classification of the labeled sensor data using global processing with a base station processor, the global processing comprising:
    forming global features from valid local measurements from a plurality of sensors;
    calculating sparse representations of global features;
    validating global features;
    classifying valid global features; and
    labeling valid global features and corresponding local features.

12. A distributed sensor system, comprising:
a plurality of sensor nodes, each node having a node processor, a plurality of sensors and a transceiver;
a non-transitory processor-readable medium including one or more instructions for:
  obtaining sensor data from a plurality of sensors at a local site;
  performing a local classification of the sensor data with local processing on the node processor, the local processing comprising:
    taking projections of the sensor data to reduce dimensionality;
    providing training sequences for each sensor;
    calculating sparse representations of features using training sequences;
    validating local measurements; and
    classifying valid local measurements;
a base station with a station processor and a transceiver; and
a non-transitory processor-readable medium including one or more instructions for:
  obtaining labeled sensor data transmitted from a plurality of sensor nodes;
  performing a global classification of the sensor data with the station processor, the global processing comprising:
    forming global features from valid local measurements from a plurality of sensors;
    calculating sparse representations of global features;
    validating global features; and
    classifying valid global features; and
    labeling valid global features and corresponding local features.

* * * * *